(12) United States Patent
Hanson et al.

(10) Patent No.: US 11,033,679 B2
(45) Date of Patent: Jun. 15, 2021

(54) FILL-FINISH CARTRIDGES FOR STERILE FLUID PATHWAY ASSEMBLIES AND DRUG DELIVERY DEVICES INCORPORATING FILL-FINISH CARTRIDGES

(71) Applicant: UNL Holdings LLC, New York, NY (US)

(72) Inventors: Ian B. Hanson, Wayne, PA (US); Paul F. Bente, IV, Wayne, PA (US); Sean M. O'Connor, West Chester, PA (US); Matthew J. Clemente, Downingtown, PA (US); Ryan M. Agard, Royersford, PA (US); Nicholas J. Ciccarelli, Philadelphia, PA (US)

(73) Assignee: UNL HOLDINGS LLC, New York, NY (US)

( * ) Notice: Subject to any disclaimer, the term of this patent is extended or adjusted under 35 U.S.C. 154(b) by 396 days.

(21) Appl. No.: 13/798,037

(22) Filed: Mar. 12, 2013

(65) Prior Publication Data

US 2013/0237916 A1 Sep. 12, 2013

Related U.S. Application Data

(60) Provisional application No. 61/609,745, filed on Mar. 12, 2012.

(51) Int. Cl.
*A61M 5/162* (2006.01)
*A61L 2/00* (2006.01)
(Continued)

(52) U.S. Cl.
CPC ............... *A61M 5/162* (2013.01); *A61L 2/00* (2013.01); *A61M 5/1452* (2013.01);
(Continued)

(58) Field of Classification Search
CPC .. A61M 2205/12; A61M 5/1452; A61M 5/24; A61M 5/28; A61M 5/14566;
(Continued)

(56) References Cited

U.S. PATENT DOCUMENTS 3,802,430 A * 4/1974 Schwebel ............... A61M 5/30
604/69
3,884,230 A * 5/1975 Wulff ................. A61M 5/31513
604/198

(Continued)

FOREIGN PATENT DOCUMENTS

CN 1671430 A 9/2005
CN 1744871 A 3/2006
(Continued)

OTHER PUBLICATIONS

European Patent Office, Communication Relating to the Results of the Partial International Search in International Application No. PCT/US2012/053241, 2 pages (dated Nov. 30, 2012).
(Continued)

*Primary Examiner* — Scott J Medway
(74) *Attorney, Agent, or Firm* — Hamilton, Brook, Smith and Reynolds, P.C.

(57) ABSTRACT

A fluid pathway assembly includes a needle insertion mechanism, a fluid conduit, and a fluid pathway connection. The fluid pathway assembly may further include a drug container to hold a drug fluid prior to initiation of the injection. The assembly may include a carrier disposed along at least a portion of the fluid pathway assembly, and/or a drug container. The fill-finish cartridge functions to retain the components of the fluid pathway assembly in a sterile condition, while allowing for easy integration of the fluid pathway assembly and the drug container into a standard fill-finish process. Methods of constructing a cartridge,
(Continued)

filling a drug container included in a cartridge, and incorporating the same into a drug delivery device are disclosed.

32 Claims, 18 Drawing Sheets

(51) Int. Cl.
  *A61M 5/158* (2006.01)
  *A61M 5/145* (2006.01)
(52) U.S. Cl.
  CPC ........ *A61M 5/14566* (2013.01); *A61M 5/158* (2013.01); *A61M 5/1626* (2013.01); *A61M 2005/1585* (2013.01); *A61M 2205/12* (2013.01); *Y10T 29/49826* (2015.01)
(58) Field of Classification Search
  CPC .......... A61M 5/158; A61M 2005/1585; A61M 2005/14252; A61M 2005/14268; A61M 5/1413
  See application file for complete search history.

(56) References Cited

U.S. PATENT DOCUMENTS

| | | | |
|---|---|---|---|
| 4,004,586 A | 1/1977 | Christensen et al. | |
| 4,673,400 A | 6/1987 | Martin | |
| 4,685,903 A | 8/1987 | Cable et al. | |
| 4,755,173 A | 7/1988 | Konopka et al. | |
| 4,840,620 A | 6/1989 | Kobayashi et al. | |
| 5,099,992 A | 3/1992 | Heimreid | |
| 5,167,816 A | 12/1992 | Kruger et al. | |
| 5,405,330 A * | 4/1995 | Zunitch | A61M 5/34 604/240 |
| 5,616,135 A | 4/1997 | Thorne et al. | |
| 5,795,339 A | 8/1998 | Erskine | |
| 5,858,001 A | 1/1999 | Tsals et al. | |
| 5,968,016 A * | 10/1999 | Yerfino | A61M 25/0637 604/177 |
| 6,248,093 B1 | 6/2001 | Moberg | |
| 6,263,641 B1 | 7/2001 | Odell et al. | |
| 6,595,956 B1 * | 7/2003 | Gross | A61M 5/14248 128/DIG. 12 |
| 6,699,218 B2 | 3/2004 | Flaherty et al. | |
| 7,063,684 B2 | 6/2006 | Moberg | |
| 7,479,135 B2 | 1/2009 | Richter et al. | |
| 7,611,503 B2 | 11/2009 | Spohn et al. | |
| 7,803,134 B2 | 9/2010 | Sharifi et al. | |
| 7,811,262 B2 * | 10/2010 | Moberg | A61J 1/1406 604/201 |
| 7,828,528 B2 * | 11/2010 | Estes | A61M 5/14244 417/43 |
| 7,828,764 B2 * | 11/2010 | Moberg | A61J 1/1406 604/155 |
| 7,846,132 B2 | 12/2010 | Gravesen et al. | |
| 7,857,131 B2 * | 12/2010 | Vedrine | A61M 5/14248 206/363 |
| 7,905,859 B2 | 3/2011 | Bynum et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,157,769 B2 | 4/2012 | Cabiri | |
| 8,167,844 B2 | 5/2012 | Dillard, III | |
| 8,187,232 B2 | 5/2012 | Chong et al. | |
| 8,900,190 B2 * | 12/2014 | Chong | A61M 5/14248 604/131 |
| 9,061,097 B2 * | 6/2015 | Holt | A61M 5/14248 |
| 9,173,997 B2 * | 11/2015 | Gross | A61M 5/14248 |
| 9,180,244 B2 * | 11/2015 | Anderson | A61M 5/14248 |
| 2004/0074076 A1 * | 4/2004 | Landau | 29/469 |
| 2004/0092878 A1 | 5/2004 | Flaherty | |
| 2006/0200073 A1 * | 9/2006 | Radmer | A61M 5/14248 604/93.01 |
| 2007/0010789 A1 | 1/2007 | Peter et al. | |
| 2007/0049865 A1 * | 3/2007 | Radmer | A61M 5/14248 604/93.01 |
| 2008/0051714 A1 * | 2/2008 | Moberg | A61M 5/1413 604/135 |
| 2008/0077116 A1 * | 3/2008 | Dailey | A61J 1/10 604/410 |
| 2008/0132842 A1 | 6/2008 | Flaherty | |
| 2008/0269687 A1 | 10/2008 | Chong et al. | |
| 2009/0076453 A1 * | 3/2009 | Mejlhede | A61M 5/142 604/151 |
| 2009/0093792 A1 * | 4/2009 | Gross | A61M 5/14248 604/518 |
| 2009/0124979 A1 | 5/2009 | Raymond et al. | |
| 2009/0204077 A1 | 8/2009 | Hasted et al. | |
| 2011/0160654 A1 * | 6/2011 | Hanson | A61M 5/1413 604/67 |
| 2011/0160669 A1 * | 6/2011 | Gyrn | A61M 5/158 604/151 |
| 2011/0166509 A1 | 7/2011 | Gross et al. | |
| 2012/0035546 A1 | 2/2012 | Cabiri | |
| 2012/0123354 A1 | 5/2012 | Woehr | |
| 2013/0085439 A1 * | 4/2013 | Sansoucy | A61M 1/3655 604/9 |
| 2014/0261758 A1 * | 9/2014 | Wlodarczyk | A61M 39/10 137/315.01 |
| 2015/0320936 A1 * | 11/2015 | Dunne | A61M 5/2033 604/199 |

FOREIGN PATENT DOCUMENTS

| | | | |
|---|---|---|---|
| CN | 101563120 A | 10/2009 | |
| CN | 101573151 A | 11/2009 | |
| EP | 1702635 A2 | 9/2006 | |
| EP | 1341569 B1 | 1/2007 | |
| EP | 1427471 B1 | 2/2008 | |
| EP | 1695727 B1 | 7/2008 | |
| EP | 1513580 B1 | 3/2009 | |
| EP | 2077128 A1 | 7/2009 | |
| EP | 2379134 A1 | 10/2011 | |
| EP | 2429612 A1 | 3/2012 | |
| EP | 2433663 A1 | 3/2012 | |
| JP | 2002-514940 A | 5/2002 | |
| WO | WO 96/21483 A1 | 7/1996 | |
| WO | WO 99/48546 A1 | 9/1999 | |
| WO | WO 2003/024504 A2 | 3/2003 | |
| WO | WO 2003/103763 A1 | 12/2003 | |
| WO | WO 2004/062714 A1 | 7/2004 | |
| WO | WO 2005/037350 A2 | 4/2005 | |
| WO | WO 2008/024808 A2 | 2/2008 | |
| WO | WO 2009/013844 | 1/2009 | |
| WO | WO 2010/077807 A1 | 7/2010 | |
| WO | WO2010/084113 | * 7/2010 | ............ A61M 5/158 |
| WO | WO 2010/084113 A1 | 7/2010 | |
| WO | WO 2010/112377 A1 | 10/2010 | |
| WO | WO 2010/132196 A1 | 11/2010 | |
| WO | WO 2011/006652 A1 | 1/2011 | |
| WO | WO 2011/007194 A1 | 1/2011 | |
| WO | WO 2011/090956 A2 | 7/2011 | |
| WO | WO 2011/121023 A1 | 10/2011 | |
| WO | WO 2011/133823 | 10/2011 | |
| WO | WO 2011/146012 A1 | 11/2011 | |
| WO | WO 2012/131044 A1 | 10/2012 | |
| WO | WO 2013/033421 A2 | 3/2013 | |
| WO | WO 2013/033467 A2 | 3/2013 | |
| WO | WO 2013/040032 A1 | 3/2013 | |
| WO | 2013/138392 | 9/2013 | |

OTHER PUBLICATIONS

European Patent Office, International Search Report in International Application No. PCT/US2012/053174, 4 pages (dated Mar. 28, 2013).

European Patent Office, International Search Report in International Application No. PCT/US2012/053241, 6 pages (dated Feb. 28, 2013).

(56) References Cited

OTHER PUBLICATIONS

European Patent Office, International Search Report in International Patent Application No. PCT/US2012/054861, 8 pages (dated Feb. 18, 2013).
European Patent Office, Written Opinion of the International Searching Authority in International Application No. PCT/US2012/053174, 6 pages (dated Mar. 28, 2013).
European Patent Office, Written Opinion of the International Searching Authority in International Application No. PCT/US2012/053241, 8 pages (dated Feb. 28, 2013).
Preliminary Amendment and Application Data Sheet Filed in National Phase of WO 2011/090956 A2 (U.S. Appl. No. 13/521,181) (dated Jul. 9, 2012).
European Patent Office, International Search Report of the International Searching Authority in International Application No. PCT/US2013/030624, 5 pages (dated Aug. 7, 2013).
European Patent Office, Written Opinion of the International Searching Authority in International Application No. PCT/US2013/030624, 7 pages (dated Aug. 7, 2013).
International Preliminary Report on Patentability in Int'l Application No. PCT/US2013/030624, titled: Fill Finish Adapters for Sterile Fluid Pathway Assemblies, dated: Sep. 25, 2014 (9 pgs).

\* cited by examiner

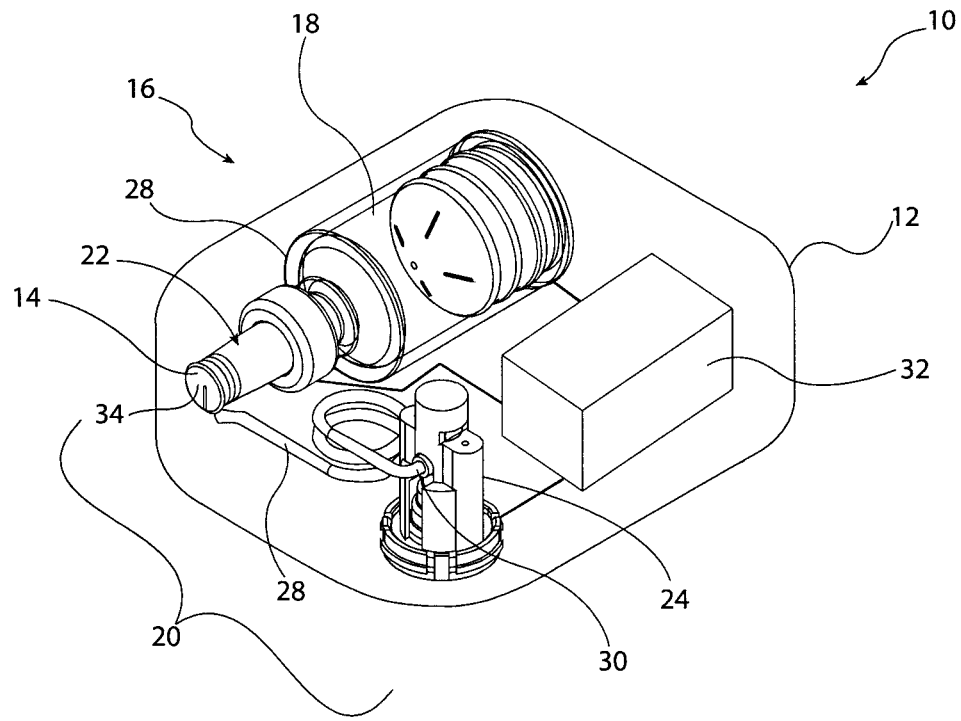

FIG. 1

| Fluid Pathway Connection with Drug Container | Fluid Pathway Connection Attachment to Needle Insertion Mechanism | Fill-Finish Cartridge Alignment | Carrier |
|---|---|---|---|
| Mounted | Snap | Axial fill and use | None |
| Integrated | Threaded | Axial fill and non-axial use | Integrated |
| Other | Interference | Non-axial fill and axial use | Fully Disposable |
| | Tongue and groove | Non-axial fill and use | Partially Disposable |
| | External support | | |
| | Other | | |

FIG. 2B

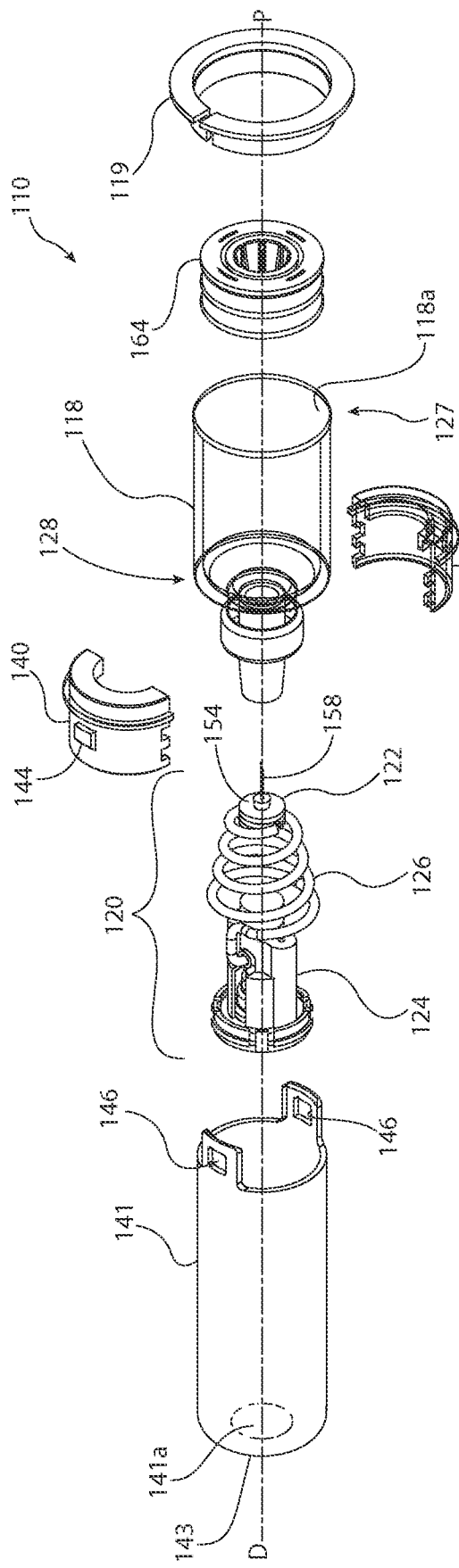
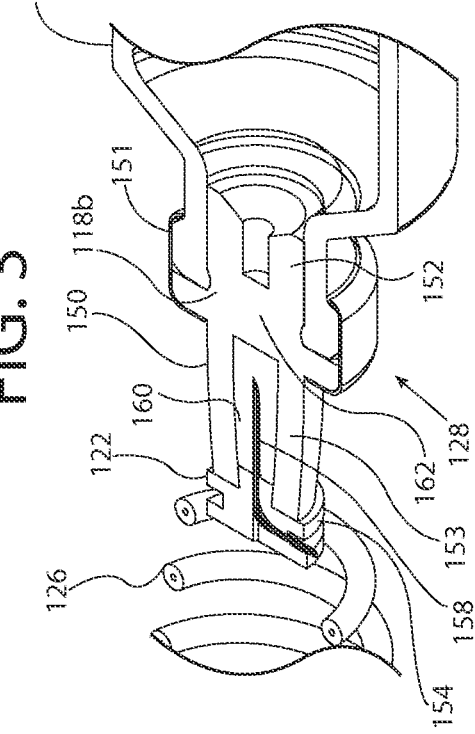
FIG. 3
FIG. 4

FILL-FINISH CARTRIDGES FOR STERILE FLUID PATHWAY ASSEMBLIES AND DRUG DELIVERY DEVICES INCORPORATING FILL-FINISH CARTRIDGES

CROSS-REFERENCE TO RELATED APPLICATIONS

This application claims priority to U.S. Provisional Application No. 61/609,745 filed Mar. 12, 2012, which is included by reference herein in its entirety for all purposes.

FIELD OF THE INVENTION

The present invention relates to sterile fluid pathway assemblies. More specifically, the embodiments of the present invention relate to fluid pathway assemblies which maintain sterility during manufacturing, fill-finish cartridges for use with such sterile fluid assemblies, fill-finish trays which facilitate the manufacture and filling of such assemblies, methods for manufacturing and filling such assemblies, and their methods of use.

BACKGROUND OF THE INVENTION

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after device sterilization but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The delivery device is filled with the drug or other solution at the point of use and injected into the patient. These devices have the disadvantage of increasing the time and difficulty of filling the device at the point of use with increased possibility of contamination of the delivery device and/or drug solution. There is a further risk of glass particles from the ampoules contaminating the drug solution when the ampoules are opened.

Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

BRIEF SUMMARY OF THE INVENTION

The inventors of the present invention have developed sterile fluid pathway assemblies which can be utilized in drug delivery devices and which can be filled with pharmaceutical treatments using standard filling equipment and systems. This advantage is enabled by the novel fill-finish cartridges of the present invention which function to maintain the sterility of the fluid pathway assemblies and allow them to nest, mount, or otherwise be removably inserted into trays for standard fill-finish processes, as discussed further below.

The embodiments of the present invention relate to fluid pathway assemblies for infusion systems which maintain sterility during manufacturing, fill-finish cartridges for use with such sterile fluid assemblies, fill-finish trays which facilitate the manufacture and filling of such assemblies, methods for manufacturing and filling such assemblies, and their methods of use. The embodiments of the present invention may provide reliable fluid pathway systems which integrate needle injection and retraction mechanism, for improved user safety, without requiring complex manufacturing processes or operational changes for pharmaceutical companies or contract drug fillers. Additionally, the embodiments of the present invention provide configurations which utilize materials and components which are readily employable for pharmaceutical use, many of which are increasingly considered off-the-shelf or standard components. Furthermore, embodiments of the present invention may provide sterile fluid pathways which may be integrated with reusable or non-reusable devices, such as infusion or injection pumps, for drug delivery of pharmaceutical treatments. The novel fill-finish cartridges of the present invention are notably able to be adapted to the fluid pathway assemblies so that they can be filled with pharmaceutical treatments in standard manufacturing fill-finish process lines, while maintaining the sterility and container integrity of the fluid pathway. The fill-finish cartridges, in connection with the fluid pathway assemblies of the present invention, can be nestled or removably housed in fill-finish trays for batch filling in standard operating processes. As such, the adaptable fill-finish cartridges and fluid pathway assemblies of the present invention may be flexibly inserted, attached, mounted, or otherwise removably positioned in fill-finish trays. These embodiments, accordingly, may provide novel and cost-efficient assemblies and cartridges which are readily integrated into drug filling processes.

In a first embodiment, the present invention provides a fluid pathway assembly which includes a needle insertion mechanism, a fluid conduit, and a fluid pathway connection. The fluid conduit is a length of flexible tubing or similar material which connects at one end to the needle insertion mechanism and at another end to the fluid pathway connection. These components are connected such that the sterility of the fluid pathway from the fluid pathway connection, through the fluid conduit, to the needle insertion mechanism is maintained. The needle insertion mechanism may itself include one or more components. In at least one embodiment, however, the needle insertion mechanism is one unified component which functions first to insert the needle for fluid delivery to a patient and then safely retract the needle at the end of drug delivery.

In a further embodiment, the fluid pathway assembly includes a drug container to hold a drug fluid prior to initiation of the injection. The drug container may be mounted to the fluid pathway connection in an aseptic manner but sealed at one end to prevent fluid transfer from the container through the fluid pathway until initiation by the user. The drug container may be, for example, a glass vial sealed with a permeable membrane that may be pierced by the fluid pathway connection upon activation by the user. In at least one embodiment, the drug container is a glass barrel tube having a permeable membrane seal at a distal end and a plunger seal, such as an elastomeric plunger seal, at a proximal end. Upon activation, the fluid pathway connection may be caused to pierce the drug container, thereby permitting fluid to flow from the container through the connection, the fluid conduit, and the needle insertion mechanism for drug delivery to the patient. The fluid pathway connection may also be comprised of one or more components. In at least one embodiment, the fluid pathway connection includes a means for mounting to the drug container, a means for connecting the fluid conduit to the drug container, and optionally a means for disconnecting the fluid conduit from the drug container. The means for mounting may be, for example, a connection collar. The means for connecting the fluid conduit to the drug container may be, for example, a needle or cannula. The means for disconnecting the fluid conduit may be, for example, a secondary retraction mechanism or a closing flange. The fluid pathway assembly may be mounted into a drug delivery device which may include other components to facilitate the activation of the device and the needle insertion, retraction, and other mechanisms of the fluid pathway assembly and the overall device. For example, the device may include a drive mechanism which connects to the plunger seal of the drug container, to force the drug fluid out of the container, through the connection, the fluid conduit, and the needle insertion mechanism for drug delivery to the patient. A number of different drive mechanisms and other known components may be utilized in this way, as would be appreciated by one having ordinary skill in the art.

A drug or pharmaceutical treatment may be filled into the drug container, in either a pre-filled or fill at time-of-use method. For example, the drug container may be configured for a pre-filled drug delivery system. In one such configuration, the drug container would have a permeable seal at a distal end and a plunger seal at a proximal end. The permeable seal may be fixedly attached, by glue or other known method of adhesion or connection such as compression fit, to the distal end of the container. The container may then be filled with a desired quantity of drug at the proximal end of the container. After completion of the filling, the plunger seal may be mounted at the proximal end of the container. As would be appreciated by one having ordinary skill in the art, this filling and assembly process may be completed under vacuum and/or a sterile environment to facilitate the aseptic manufacturing of the safety syringe. These safety syringes are configured such that they may readily be manufactured individually, or in a group, as is the case in a tray-based filling process. Integration of the fluid pathway assemblies into such standard fill-finish processes is enabled, at least in part, by the novel fill-finish cartridges of the present invention.

Accordingly, in another embodiment the present invention relates to a fill-finish cartridge which includes a cartridge barrel, a fluid pathway assembly, and a drug container. The fluid pathway system includes the components discussed above and may be configured to reside within the cartridge barrel in a manner which maintains the sterility of the fluid path within the fluid pathway assembly. The fill-finish cartridge may further include a connection collar to connect the cartridge barrel to the drug container. As described in further detail below, the cartridge barrel may be one or more pieces such that the cartridge barrel is expandable or adjustable. The cartridge barrel may be configured to retain the fluid pathway assembly and connect to the drug container, or a connection collar may be utilized for the latter purpose. Furthermore, the fill-finish cartridge may include a flange at a proximal end of the drug container. The flange may be a fixed flange or a removable flange. The flange may consist of a number of known materials including, but not limited to, glass and plastic. The fill-finish cartridge functions to retain the components of the fluid pathway assembly in a sterile condition, while allowing for easy integration of the fluid pathway assembly and the drug container into a standard fill-finish process. The fill-finish cartridges, including the fluid pathway assembly and the drug containers, can be integrated into standard trays. For example, these cartridges, assemblies, and containers can be removably mounted into standard filling trays for filling in automated assembly and drug filling lines. The containers can then be filled with a pharmaceutical drug or treatment, and then sealed by insertion of a plunger seal into the proximal end of the drug container.

In yet another embodiment, the present invention relates to a method of assembling a fluid pathway assembly which includes the steps of: connecting a fluid pathway connection to a proximal end of a fluid conduit and connecting a needle insertion mechanism to a distal end of said fluid conduit, wherein said connections are made within a sterile environment. In another embodiment, the present invention relates to a method of manufacturing a fill-finish cartridge which includes the steps of inserting a sterile fluid pathway assembly into a proximal end of a cartridge barrel, such that the fluid pathway assembly is caused to mount within an inner diameter of the cartridge barrel; and connecting a drug container which includes a permeable seal at a distal end of the container to the proximal end of the cartridge barrel, wherein the connection between the drug container and the cartridge barrel places a fluid pathway connection of the fluid pathway assembly substantially adjacent to the permeable seal of the drug container but does not cause the seal to be pierced until activation by the user. The method of manufacturing may further include the steps of filling the drug container from an opening at the proximal end; and then movably sealing the proximal end of the drug container by inserting a plunger seal.

In a further embodiment, the present invention relates to the method of using the fluid pathway assembly having a needle insertion mechanism, a fluid conduit, a fluid pathway connection, and a drug container, which method includes the steps of: filling the drug container with a pharmaceutical drug; mounting the needle insertion mechanism to a first location of a drug delivery device; mounting the drug container to a second location of the drug delivery device; triggering the fluid pathway connection to pierce a permeable seal at a distal end of the drug container; triggering the needle insertion mechanism to insert a cannula into a patient; activating a drive mechanism to force the pharmaceutical drug out of the drug container and through the primary container connect, a fluid conduit, and the cannula of the needle insertion mechanism for drug dispersal into the patient. Upon completion of drug delivery, the method of use may further include the step of triggering the needle insertion mechanism to retract the cannula from the patient. The cannula may be a rigid needle, a flexible tube cannula, or a number of other known conduits for injection and/or drug delivery.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 1 is an isometric view of a drug delivery device incorporating an embodiment of a fill-finish cartridge according to aspects of the invention;

FIG. 2B is a chart of exemplary combinations of components of a fill-finish cartridge according to aspects of the invention;

FIG. 3 is an exploded isometric view of a fill-finish cartridge, according to an embodiment of the invention;

FIG. 4 is a enlarged fragmentary isometric cross-sectional view of the fluid pathway connection of the fill-finish cartridge shown in FIG. 3, cross-hatching being eliminated for the purposes of clarity;

DETAILED DESCRIPTION OF EMBODIMENTS

Figure 2A:
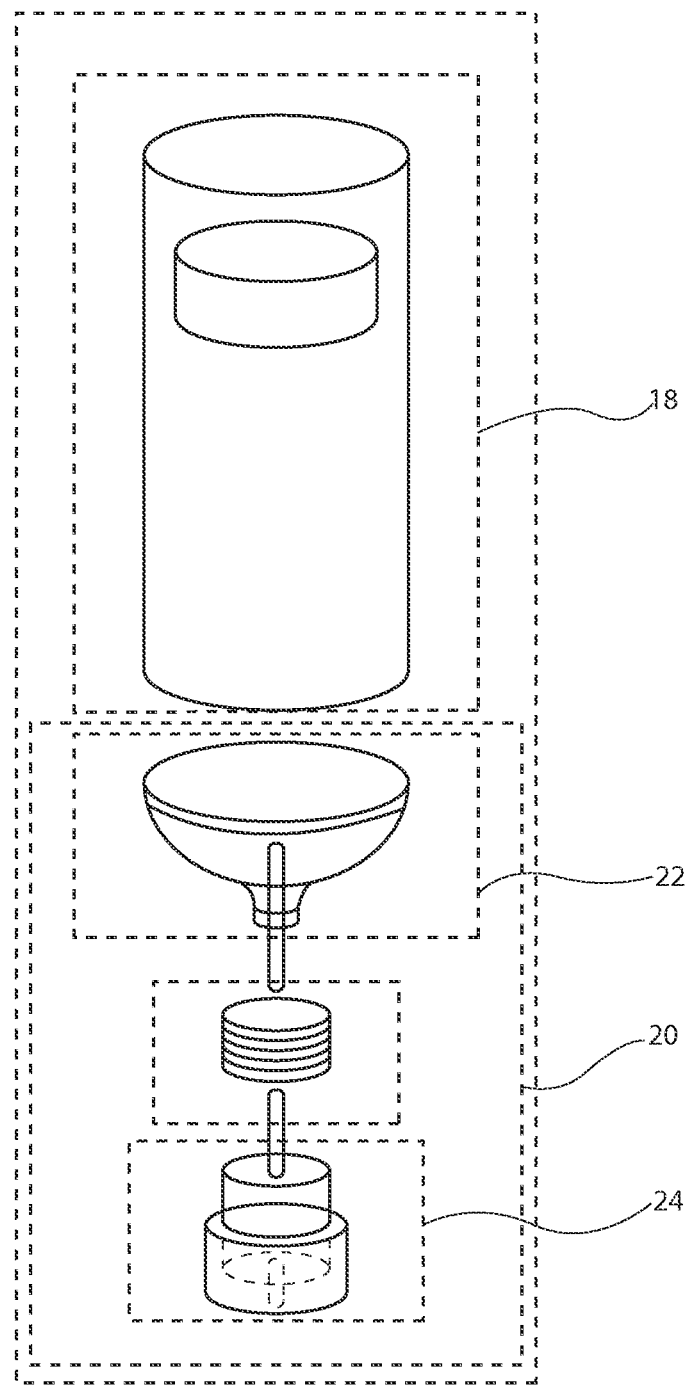
FIG. 2A is a schematic representation of an exemplary fill-finish cartridge of the present invention.

The inventors of the present invention have developed sterile fluid pathway assemblies which can be utilized in drug delivery devices and which can be filled with pharmaceutical treatments using standard filling equipment and systems. This advantage is enabled by the novel fill-finish cartridges of the present invention which function to maintain the sterility of the fluid pathway assemblies and allow them to nest, mount, or otherwise be removably inserted into trays for standard fill-finish processes, as discussed further below. The embodiments of the present invention may be integrated into advanced drug delivery devices, such as injection and/or infusion pumps, which require sterile fluid pathways.

As used herein to describe the fluid pathway assemblies, fill-finish cartridges, drug delivery devices, or any of the relative positions of the components of the present invention, the terms "axial" or "axially" refer generally to a longitudinal axis "A" around which drug container is preferably formed although not necessarily symmetrically therearound. The term "radial" refers generally to a direction normal to axis A. The terms "proximal," "rear," "rearward," "back," or "backward" refer generally to an axial direction in the direction of the drug container. The terms "distal," "front," "frontward," "depressed or "forward" refer generally to an axial direction in the direction of the fill-finish cartridge. As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration. As used herein, the term "fluid" refers primarily to liquids, but can also include suspensions of solids dispersed in liquids, and gasses dissolved in or otherwise present together within liquids inside the fluid-containing portions of syringes.

Turning to FIG. 1, there is illustrated a schematic representation of an example of a drug delivery device 10 incorporating aspects of the invention. The device 10 includes a housing 12 having an activation mechanism 14. For ease of understanding, the housing 12 is shown schematically. In accordance with the invention, the device further includes a fill-finish cartridge 16. The fill-finish cartridge 16 includes a drug container 18, a fluid pathway assembly 20 including a fluid pathway connection 22 and a needle insertion mechanism 24. The fluid pathway assembly 20 may include further structure that facilitates disposition of various components, including, for example, a fluid conduit 26. The fluid pathway connection 22 is disposed substantially adjacent a distal end 28 of the drug container 18, and the needle insertion mechanism 24 is disposed substantially adjacent a distal end 30 of the fluid pathway connection 22. In the illustrated embodiment, the drug container 18 is generally horizontally positioned and perpendicular from a vertically positioned needle insertion mechanism 24. It will be appreciated, however, that the components may be positioned in any appropriate manner.

Administration of a drug contained in the drug container 18 may be initiated by the activation mechanism 14. The activation mechanism 14 may include, for example, activation mechanisms that are manually actuated by a user, or that are automatically actuated by, for example, a power and control module 32 that may include, by way of further example, a microprocessor or other automatic administration arrangement with appropriate connections. In this embodiment, the activation mechanism 14 is a button 34 that may be disposed, for example, along an outer surface of the housing 12, and may be selectively depressed by the user. It will be appreciated that the drug delivery device 10 as well as the activation mechanism 14 may be of any appropriate design.

The power and control module 32, if included, may include a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control module 32 controls several device interactions with the user and may interface with one or more other components of the drug delivery device 10. In one embodiment, the power and control module 32 may identify when an on-body sensor and/or the activation mechanism 14 have been activated. The power and control module 32 may also interface with a status indicator, which may be a transparent or translucent material which permits light transfer, to provide visual feedback to the user. The power and control module 32 may interface with a drive mechanism and/or the integrated sterile fluid pathway connection and drug container 18 through one or more interconnects to relay status indication, such as activation, drug delivery, and/or end-of-dose, to the user. Such status indication may be presented to the user via tactile feedback, such as vibration; auditory tones, such as through the audible alarms; and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may also maintain the energy stored in the power source during storage, transport, and the like.

The power and control module 32 may be configured to provide a number of different status indicators to the user. For example, the power and control module 32 may be configured such that after the on-body sensor and/or trigger mechanism have been pressed, the power and control module 32 provides a ready-to-start status signal via the status indicator if device start-up checks provide no errors. After providing the ready-to-start status signal and, in an embodiment with the optional on-body sensor, if the on-body sensor remains in contact with the body of the user, the power and control module 32 will power the drive mechanism to begin delivery of the drug treatment through the integrated sterile fluid pathway connection 22 and sterile fluid conduit 26. In a preferred embodiment of the present invention, the insertion mechanism 24 and the drive mechanism may be caused to activate directly by user operation of the activation mechanism 14. The integrated sterile fluid pathway connection is connected (i.e., the fluid pathway is opened) by the pneumatic force of the drug fluid within the drug container 18 created by activation of the drive mechanism, as is detailed further herein. During the drug delivery process, the power and control module 32 is configured to provide a dispensing status signal via the status indicator. After the drug has been administered into the body of the user and after the end of any additional dwell time, to ensure that substantially the entire dose has been delivered to the user, the power and control module 32 may provide an okay-to-remove status signal via the status indicator. This may be independently verified by the user by viewing the drive mechanism and delivery of the drug dose within the drug container through a window of the pump housing 12. Additionally, the power and control module 32 may be configured to provide one or more alert signals via the status indicator, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a prolonged depression (i.e., pushing) of the activation mechanism 14 of the drug delivery device 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

When included, the power and control module 32 may include a processor (not shown) and a memory component (not shown). The processor may be microprocessors or other processors as known in the art. In some embodiments the processor may be made up of multiple processors. The processor may execute instructions for generating administration signal and controlling administration of a drug contained in the drug container 18. Such instructions may be read into or incorporated into a computer readable medium, such as the memory component or provided external to processor. In alternative embodiments, hard-wired circuitry may be used in place of or in combination with software instructions to implement drug administration. Thus, embodiments are not limited to any specific combination of hardware circuitry and software.

The term "computer-readable medium" as used herein refers to any medium or combination of media that participates in providing instructions to processor for execution. Such a medium may take many forms. The memory component may include any form of computer-readable media as described above. The memory component may include multiple memory components.

The power and control module 32 may be enclosed in a single housing. In alternative embodiments, the power and control module 32 may include a plurality of components operably connected and enclosed in a plurality of housings.

The power and control module 32 may be configured to generate an administration signal as a function of user actuation, preprogrammed actuation or remote actuation. The power and control module 32 may be communicatively coupled to fill-finish cartridge 16, and/or the drug container 18, the fluid pathway connection 22, and/or the needle insertion mechanism 24 individually.

In accordance with an aspect of embodiments of the invention, in the illustrated embodiment, actuation of the activation mechanism 14, here, depression of the button 34, results in engagement of the fluid pathway connection 22, as will be discussed in greater detail below. This same action by the user may trigger the needle insertion mechanism 24 to inject a needle or cannula into the patient, as will likewise be explained in greater detail below. Thus, actuation of activation mechanism 14 results in the completion of a drug pathway from the drug container 18 through the fluid pathway connection 22, the fluid conduit 26, and the needle insertion mechanism 24 to the patient (not shown). Actuation of the activation mechanism 14 may also result in a drive mechanism acting upon structure associated with the drug container 18 to force fluid through the sterile pathway. In an embodiment of the present invention, the needle insertion mechanism 24 may be triggered to retract the needle from the patient, giving a clear end of dose delivery indication upon completion of drug delivery. The housing 12 may additionally include, for example, a window through which the drug container 18 may be viewed to confirm drug delivery.

According to an aspect of embodiments of the invention, the fill-finish cartridge 16 is constructed and filled prior to assembly into the housing 12 of the drug delivery device 10. In this regard, the fill-finish cartridge 16 is sufficiently robust to withstand procedures for sterilizing the fill-finish cartridge 16, in some embodiments prior to fill, and in some embodiments after fill. After the sterile construction and filling of the fill-finish cartridges 16, the device may be positioned as needed within a drug delivery device 10. In any event, the sterility of the fluid pathway assembly 20 and the drug container 18 are maintained through aspects of the assembly, filling, and manufacturing processes. Final assembly of the drug delivery device 10 can thus be performed outside of a sterile environment. Because only the components of the sterile fluid pathway assembly 20 need to be, and have been, sterilized, the remainder of the drug delivery device 10 does not need sterilization (i.e., terminal sterilization). This provides a number of advantages. Novel embodiments of the present invention may also alleviate the need to fill the drug delivery device at time-of-use, although some embodiments of the present invention may be utilized in devices configured for time-of-use filling as well.

According to another aspect of embodiments of the invention, various embodiments of individual components of the fill-finish cartridge 16 may be assembled in various configurations to provide various embodiments of the fill-finish cartridge 16. The following disclosures assigned to the assignee of this disclosure disclose exemplary structures of individual elements that may be incorporated into the fill-finish cartridge 16, and are incorporated herein by reference for everything disclosed therein: U.S. application Ser. No. 13/600,114 filed Aug. 30, 2012; U.S. application Ser. No. 13/599,727 filed Aug. 30, 2012; U.S. application Ser. No. 13/612,203 filed Sep. 12, 2012; and Ser. No. 13/796,156 filed Mar. 12, 2013. FIG. 2A is a chart of examples of variables for possible structures of connections between individual components that may yield various configurations of embodiments of fill-finish cartridges 16, while FIG. 2B shows an example of a fill-finish cartridge 16 identifying aspects referenced in FIG. 2A. For ease of understanding, the same reference numbers are utilized as in FIG. 1. The individual components, as well as the interactions and connections between the individual components may have various designs. For example, the needle insertion mechanism 24 may be of any suitable design. Similarly, the container 18 and the fluid pathway connection 22 may each be of any appropriate design.

Likewise, the interactions between the components may be of any appropriate design. For example, the engagement of the fluid pathway connection 22 with the drug container 18 may include a threaded or snap connection, an interference fit, or an external support or other arrangement, so long as a tight seal is obtained. Similarly, the engagement of the fluid pathway connection 22 with the needle insertion mechanism 24 may include a threaded or snap connection, an interference fit, a tongue and groove arrangement, an external support, or some other arrangement including, but not limited to, utilizing a fluid conduit between the fluid pathway connection 22 and the needle insertion mechanism 24 for the connection. Moreover, in some embodiments, the engagement of the fluid pathway connection 22 with the needle insertion mechanism 24 may be disassembled following the fill-finish process in order to permit the needle insertion mechanism 24 to be oriented other than axially with the remainder of the fill-finish cartridge 16, so long as the sterile fluid connection is maintained.

In various embodiments, the fill-finish cartridge 16 may be maintained with the components in axial alignment during the fill-finish process, as well as in use with a drug delivery device 10. That is, for example, the needle insertion mechanism 24 may be disposed axially with the remainder of the fill-finish cartridge 16 during both the fill-finish process, such as is shown in FIG. 2B, and in use in a drug delivery. In other embodiments, the fill-finish cartridge 16 may be maintained with the components in axial alignment during the fill-finish process, such as is illustrated in FIG. 2B, while the components may be maintained in other than axial alignment in use with a drug delivery device 10. For example, as illustrated in FIG. 1, the needle insertion mechanism 24 is disposed spaced from the fluid pathway connection 22 and the drug container 18, and at a 90° orientation. In other embodiments, the fill-finish cartridge may be maintained with the components in other than axial alignment during the fill-finish process, yet be axially aligned in use with a drug delivery device 10. In other embodiments, the fill-finish cartridge 16 may be maintained with the components in other than axial alignment during both the fill-finish process and in use with a drug delivery device 10.

Further, while not included in all embodiments, in order to provide added structural integrity to the fill-finish cartridge 16, a carrier may be provided, as will be explained in more detail below. Such a carrier may be integrated with the structure of the fill-finish cartridge 16 such that it is maintained about or along at least a portion of the fill-finish cartridge 16 in the drug delivery device 10, or such a carrier may be fully or partially disposable. A carrier may perform a number of functions, such as, the maintenance of the relative positions of various of the fill-finish cartridge components during assembly, a fill-finish process, or other operations performed on the fill-finish cartridge or a drug delivery device incorporating the same; a carrier or a portion of a carrier may be utilized in the interaction of the fill-finish cartridge with a drug delivery device 10, such as, in attachment of the fill-finish cartridge 16 into a drug delivery device 10 or in connection with operation of a drug delivery device 10. More detailed explanations of various examples of such structures in varied configurations follow; it is not the intention to limit the structures to those particular configurations. Rather, the individual arrangements explained are provided as examples of various possible configurations and structures within the purview of this disclosure.

FIG. 3 shows an exploded view of one embodiment of the fill-finish cartridge 116 of the present invention. For ease of understanding, the number utilized in FIG. 1 are utilized in further examples of embodiments of the invention with numerical prefixes; in this embodiment, 1XX will be utilized. The fill-finish cartridge 116 of this embodiment includes a fluid pathway assembly 120 connected to a drug container 118.

The fluid pathway assembly 120 includes a needle insertion mechanism 124 coupled to a fluid pathway connection 122 by a fluid conduit 126. A proximal end of the needle insertion mechanism 124 is connected to a distal end of a fluid conduit 126, which is connected at its proximal end to the fluid pathway connection 122.

The needle insertion mechanism 124 may be of any appropriate design so long as it may be sterilized prior to the placement of the fill-finish cartridge 116 in a drug delivery device. Examples of such needle insertion mechanisms 124 for implants and liquid drugs and are disclosed in U.S. application Ser. No. 13/599,727 filed Aug. 30, 2012, which is assigned to the assignee of this application and is incorporated herein by reference for everything disclosed therein. It will be noted that the needle insertion mechanism 124 of FIG. 3 includes an axial structure, such that the administration needle (not visible in FIG. 3) extends axially from a distal end of the fill-finish cartridge 116 for administration. It will be appreciated, however, that a needle insertion mechanism 124 that is disposed at an angle to an axis of the fluid pathway connection 122 and/or drug container 118 could alternately be utilized.

The components of the fluid pathway assembly 120, including the needle insertion mechanism 124, the fluid pathway connection 122, and the fluid conduit 126 are formed of materials that may be sterilized by conventional sterilization techniques and machinery. The fluid conduit 126 may be formed of any appropriate material, for example, a length of flexible tubing, such as plastic tubing. It will be appreciated, however, that fluid pathway connection 122 and the needle insertion mechanism 124 may be directly attached in some embodiments (not illustrated in FIGS. 3 and 4).

The components of the fluid pathway assembly 120 may be sterilized in advance of such connections, or may be connected prior to sterilization as a unified component. If sterilized in advance of such connections, the fluid pathway assembly 120 may include an additional seal at the fluid pathway connection 122, such as a permeable seal that may be pierced during assembly or actuation (not illustrated).

The drug container 118 of this and each of the embodiments may be of any appropriate material and of any appropriate shape and size, and may include a seal to maintain the integrity and sterility of a drug contained therein. For example, the drug container 118 may be formed of glass, plastic, or other appropriate material. The drug container 118 of this and each of the embodiments may include structure that facilitates handling, mounting within a drug delivery device, sterilization, and/or interface with other components of the fill-finish cartridge 116. For example, a flange 119 may be provided at any appropriate location along the drug container 116. Such a flange 119 may be integrally formed with the drug container 118 or may be a separate element that is secured to the drug container. In the illustrated embodiment, the flange 119 is a separate component that is coupled to a proximal end of the drug container 118.

It will be appreciated that any appropriate drive mechanism may be provided for moving the medication from the drug container 118 to the fluid pathway assembly 120 in embodiments of the invention. For example, U.S. application Ser. No. 13/600,114 filed Aug. 30, 2013, discloses an embodiment of a drive mechanism associated with a drug container, and is incorporated herein by reference for everything disclosed in that application.

In order to facilitate both filling the drug container 118 and administering medication from the drug delivery container, the drug container 118 may include openings 118a, 118b at the proximal and distal ends 127, 128, respectively. In order to seal the drug container 118, a permeable seal 150 may be provided at a distal end 128 of the drug container 118. In this way, once filled, a drug contained within the drug container 118 may be maintained in a sterile environment until such time as the seal 150 is pierced by the fluid pathway connection 122 to complete the fluid pathway. The permeable seal 150 may be of any appropriate design and material.

The distal end 128 of the drug container 118 may be assembled with the fluid pathway assembly 120 for sterilization prior to or after fill, as will be explained in greater detail below. FIG. 4 shows an enlarged cross-sectional view of the fluid pathway connection 122 and the permeable seal 150 of FIG. 3, after these components are assembled and ready for sterilization. While the permeable seal 150 may be a single thin membrane 162 or the like across the opening 118b at the distal end 128 of the drug container 118, the permeable seal 150 may include further structure that facilitates connection with the drug container 118 and/or the fluid pathway connection 122. As shown, in at least one embodiment of the present invention, the permeable seal 150 is in the form of a container tip which caps the drug container 118, as well as provides support for the fluid pathway connection 122. In this embodiment, the permeable seal 150 may include a portion 152 that rests inside the drug container 118, providing a mating surface to mount the permeable seal 150 to the drug container 118. To assist in maintaining the connection of the seal 150 with the drug container 118 a cap 151 may be provided about portions of the permeable seal 150 and the drug container 118, such as around a lip on the drug container 118. Such a cap 151 may be of any appropriate material, such as a foil. While the drug container 118 necks in at the interface with the permeable seal 150, it will be appreciated that alternate designs may likewise be provided.

The permeable seal 150 may also have an extension 153 which facilitates mounting with the fluid pathway connection 122. In the embodiment shown in FIG. 4, the fluid pathway connection 122 includes a hub 154 through which a cannula 158 may extend. It will be appreciated by those of skill in the art that, as used herein the term "cannula" 158 includes a needle or a cannula that may be operative to provide the required fluid connection. The fluid conduit 126 is fluidly connected to the cannula 158 as it extends from a surface of the hub 154. The hub 154 of the fluid pathway connection 122 may be employed, as shown here, to mount, attach, or otherwise connect with the extension 153 of the permeable seal 150, the proximal end of the cannula 158 being disposed within a bore 160 of the extension 153. Prior to the completion of a fluid pathway between the drug container 118 and the fluid conduit 126, the cannula 158 is held in position as illustrated in FIG. 4.

The permeable seal 150 has a portion that acts as a membrane 162 that may be pierced by the cannula 158. In the embodiment of FIGS. 3 and 4, the membrane 162 is disposed generally perpendicular to the cannula 158 to close off the drug container 118 from the fluid pathway connection 122, thereby blocking the fluid pathway from the drug container 118 to the fluid conduit 126. Upon activation by the user, a portion of the permeable seal 150 blocking the drug container 118, here, membrane 162, is caused to be pierced by the cannula 158 of the fluid pathway connection 122, thereby completing the fluid pathway and permitting drug fluid to pass from the container 118 to the cannula 158 and the fluid conduit 126, and on to the needle insertion mechanism 124. In order to facilitate piercing, the extension 153 of the permeable seal 150 may bow outward in response to sufficient axial pressure, for example, to allow the cannula 158 to pierce the membrane 162 to complete the fluid pathway.

Accordingly to another aspect of embodiments of the invention, the drug container 118, fluid pathway connection 122, and the needle insertion mechanism 124 of the fill-finish cartridge 116 exhibit sufficient structural integrity to be utilized in a fill-finish process and to be assembled into a housing of a drug delivery device. It will be appreciated that any appropriate fluid pathway connection 122 may be incorporated into embodiments of the invention. For example, a mounted fluid pathway connection, such as is disclosed, for example, in U.S. application Ser. No. 13/612,203 filed Sep. 12, 2012, may be utilized. Likewise, an integrated fluid pathway connection, such as is disclosed, for example, in U.S. application Ser. No. 13/796,156 filed Mar. 12, 2013, and may be utilized. Both of these applications are assigned to the assignee of this application and are incorporated herein by reference.

Similarly, it will be appreciated that any appropriate connection may be provided between the fluid pathway connection 122 and the needle insertion mechanism 124. While examples of some connections are disclosed in detail herein, it is not the applicant's intention to limit the invention. Such a connection may include, for example, a snap connection (see FIGS. 21-23), a threaded connection (see FIGS. 16-20), an interference connection, a tongue and groove connection, an external support (see FIG. 3), or other appropriate connection.

Returning to FIG. 3, In order to provide further structural integrity to such an interface between the fluid pathway connection 122 and the permeable seal 150, and/or between the fluid pathway connection 122 and the needle insertion mechanism 124, a carrier 142 may be provided. The carrier 142 of this embodiment includes a connection collar 140 and a barrel 141. For manufacturing purposes, the connection collar 140 may itself include multiple components, as illustrated in FIG. 3, that may be coupled together about the fluid pathway connection 122, the permeable seal 150, and a portion of the drug container 118 by any appropriate mechanism. It will be appreciated, however, that a unitary connection collar 140 could alternately be provided. It will further be appreciated that the connection collar 140 may not be required or desirable in all embodiments, and that such a connection collar 140 may be provided as an integrated part of the design, or may be fully or partially disposable during the assembly or sterilization processes.

Further structural integrity may be provided by the barrel 141, which may support the fluid pathway assembly 120 during the sterilization and assembly processes. While any appropriate coupling may be provided, the connection collar 140 may facilitate coupling of the barrel 141 about the fluid pathway assembly 120. In the illustrated embodiment, the connection collar 140 includes a pair of protrusions 144 (only one being visible in FIG. 3) that mate with a pair of recesses 146 in the barrel 141. As with the connection collar 140, it will further be appreciated that the barrel 141 may not be required or desirable in all embodiments, and that such a barrel 141 may be provided as an integrated part of the design, or may be fully or partially disposable during the assembly or sterilization processes. In order to permit the needle insertion mechanism 124 to operate to administer medication, the barrel 141 may include an opening 141a through which an administration needle may extend during use.

Figure 5:
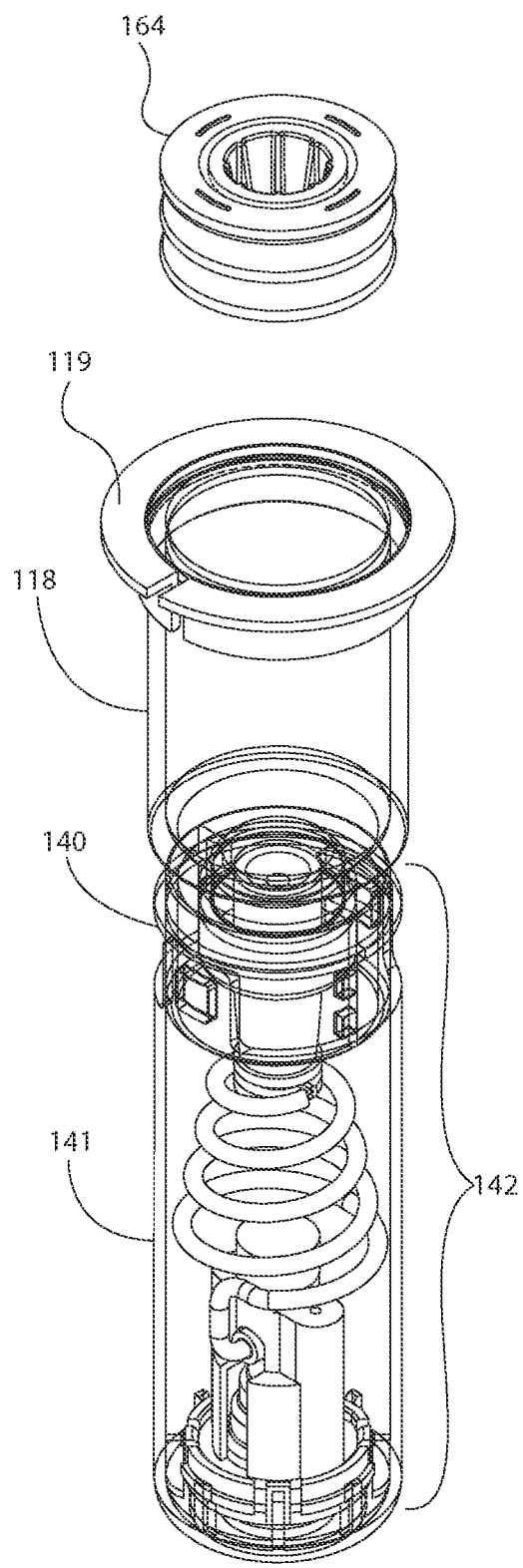
FIG. 5 is an isometric view of the fill-finish cartridge of FIG. 3 before insertion of a plunger seal, elements of FIG. 5 being shown in partial transparency.
Figure 6:
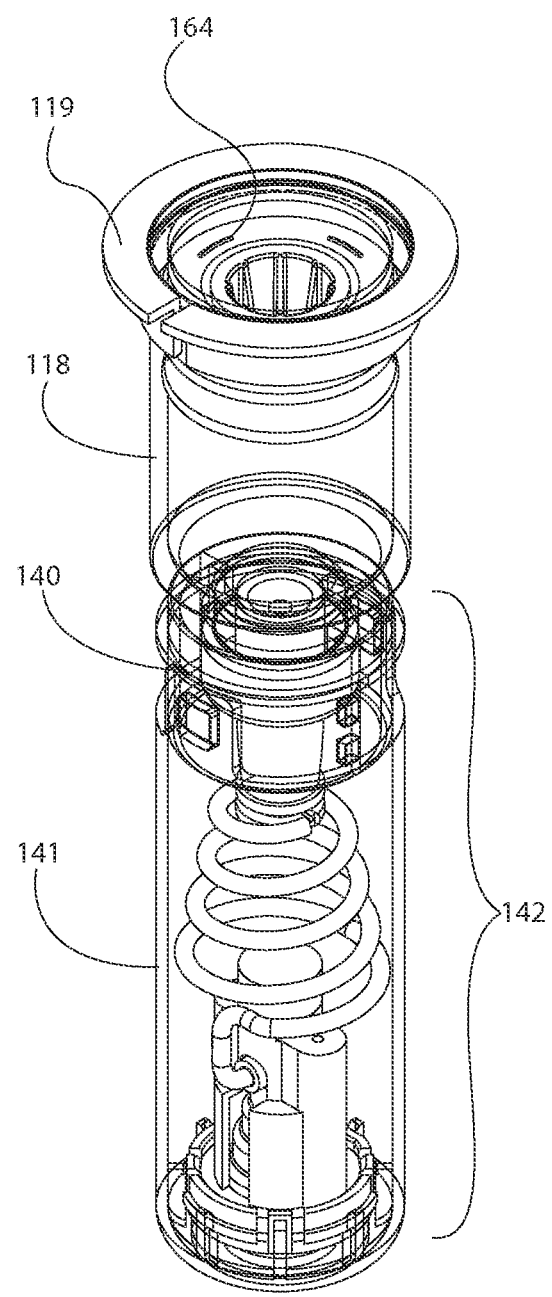
FIG. 6 is an isometric view of the fill-finish cartridge of FIG. 3 after insertion of a plunger seal, elements of FIG. 6 being shown in partial transparency.

For operational efficiency, the needle insertion mechanism 124 may be coupled to the fluid pathway connection 122, and the fluid pathway connection 122 may be connected to the permeable seal 150 with the needle insertion mechanism 124 maintained in the non-piercing configuration through the sterilization, filling, and assembly processes. In this way, the fill-finish cartridge 116 may appear as shown in FIG. 5, with the fluid pathway assembly 120 residing entirely hidden from the external environment by the carrier 142. Once the drug container 118 is filled with a pharmaceutical treatment, a seal 164 may be provided in the proximal end 127 of the drug container 118 to provide a closed fill-finish cartridge 116 that may be inserted into an appropriate drug delivery device. In the embodiment illustrated in FIGS. 5-6, an elastomeric plunger seal 164 is inserted into the proximal end 127 of the drug container 118. It will be appreciated, however, that other appropriate sealing arrangement may be provided.

According to another aspect of the invention, the fluid pathway assemblies may be maintained in a sterile condition and the drug containers of each assembly may be filled with a pharmaceutical compound aseptically using processes similar to those known in the art. After a pharmaceutical treatment is filled into the drug container and the container is sealed, for example with the plunger seal 164 of the embodiment of FIGS. 3-6, the fill-finish cartridge 116 may be removed from the sterile filling environment without comprising the sterility or container integrity of the drug container 118, fluid pathway assembly 120, or their individual components.

Alternatively, the fill-finish process may be such that the plunger seal 164 is inserted to the proximal end of the drug container 118 prior to filling the container 118 with a pharmaceutical treatment. In such an embodiment, the pharmaceutical treatment may be filled from the distal end 128 of the drug container 118 prior to insertion and connection of the fluid pathway connection 122 and the fluid pathway assembly 120. Accordingly, the fill-finish cartridges of the present invention enable the fluid pathway assemblies of the present invention to be filled with pharmaceutical treatments in standard fill-finish processes, greatly reducing the complexities associated with manufacturing and operation of the components and the drug delivery devices in which they are incorporated.

Figure 8:
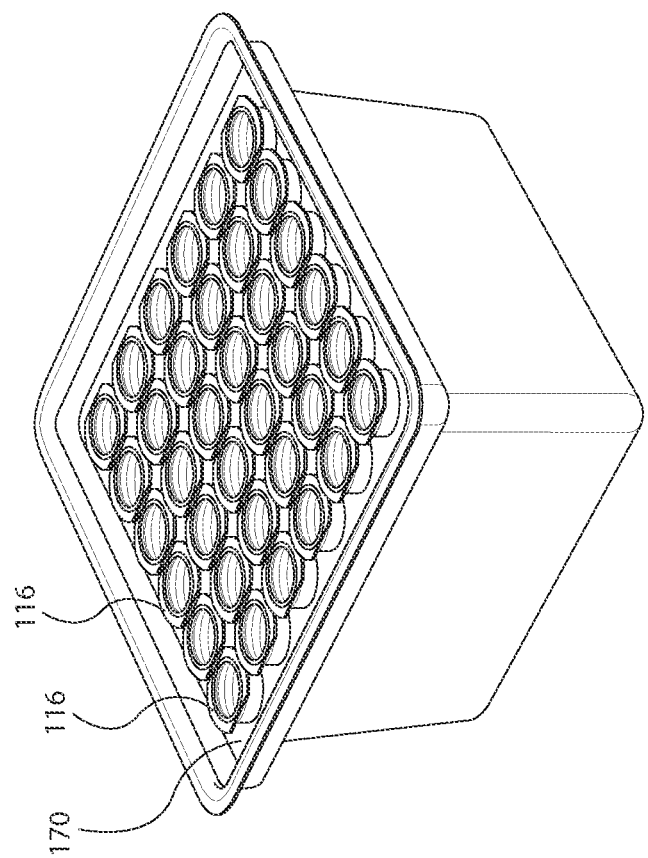
FIG. 8 is an isometric view of the a tray of FIG. 7 in an assembled form and holding a plurality of fill-finish cartridges for use in a fill-finish process.
Figure 7:
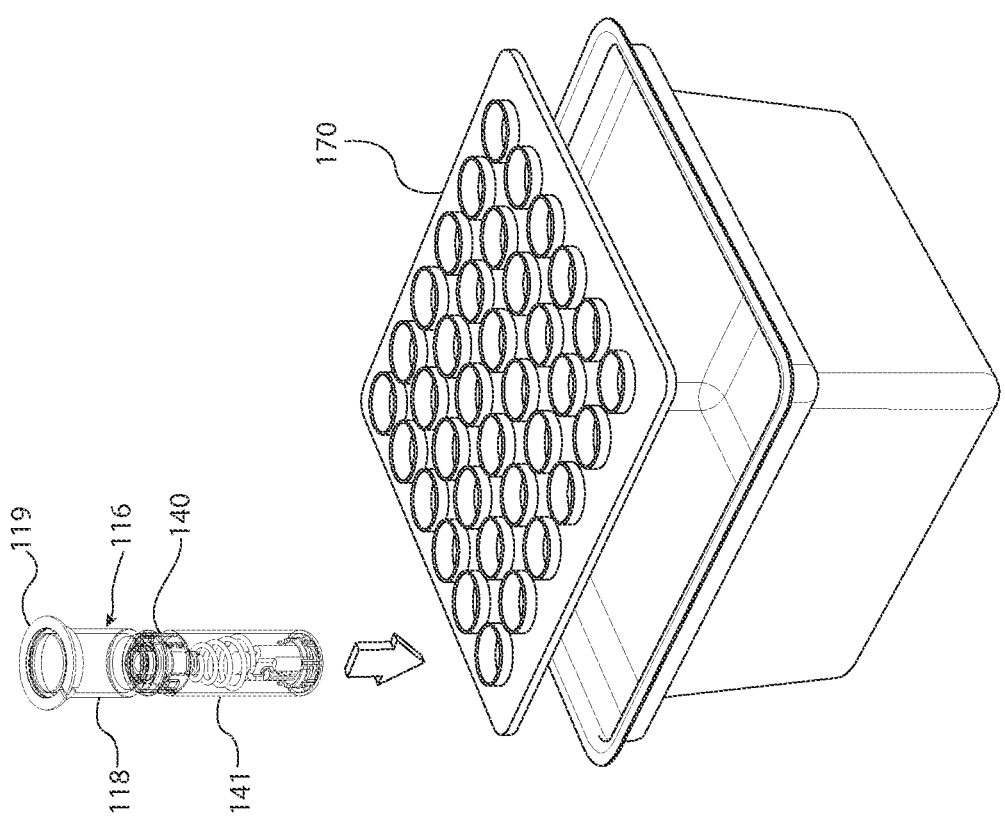
FIG. 7 is an exploded isometric view of a tray which may be utilized to retain a plurality of fill-finish cartridges for use in a fill-finish process, elements of FIG. 7 being shown in partial transparency.

According to another aspect of the invention, embodiments of the fill-finish cartridges of the present invention may enable the fluid pathways assemblies to be filled in standard fill-finish processes. In this regard, the fill-finish cartridges may utilize existing or standardized fill-finish equipment. A plurality of fill-finish cartridges 116, such as is illustrated in FIGS. 3-6, for example, may be removably mounted, mated, inserted, or otherwise placed into a standard fill-finish tray 170, such as illustrated in FIGS. 7-8, for filling with pharmaceutical treatments. As explained above, the flange 119 of the drug container 118 may assist in placement and handling of the fill-finish cartridges 116. The fill-finish tray 170 illustrated in FIGS. 7-8 is configured to hold thirty-six drug containers, here, fill-finish cartridges 116, but trays of any configuration or capable of holding any number of containers may be utilized.

According to another aspect of the invention, fill-finish cartridges may be configured to be fixed cartridges or adjustable cartridges. For example, the cartridges may have a flexible or adjustable portion that enables them to bend, rotate, expand, or contract to fit a number of different fluid pathway assemblies or to mate with fill-finish processing trays of different dimensions.

According to yet another aspect of the invention, components of some embodiments of the fill-finish cartridges may be incorporated into the drug delivery devices, while in other embodiments, components of the fill-finish cartridges may be utilized for the fill-finish process and then discarded upon mounting the fluid pathway assembly and drug container into a drug delivery device. For example, in an embodiment such as is illustrated in FIGS. 3-6 is utilized as shown in FIG. 1, by removing the barrel, the connection collar may be utilized to mount and/or brace the drug container into position within the drug delivery device, while the needle insertion mechanism is mounted remotely from and 90° to the drug container.

Figure 9:
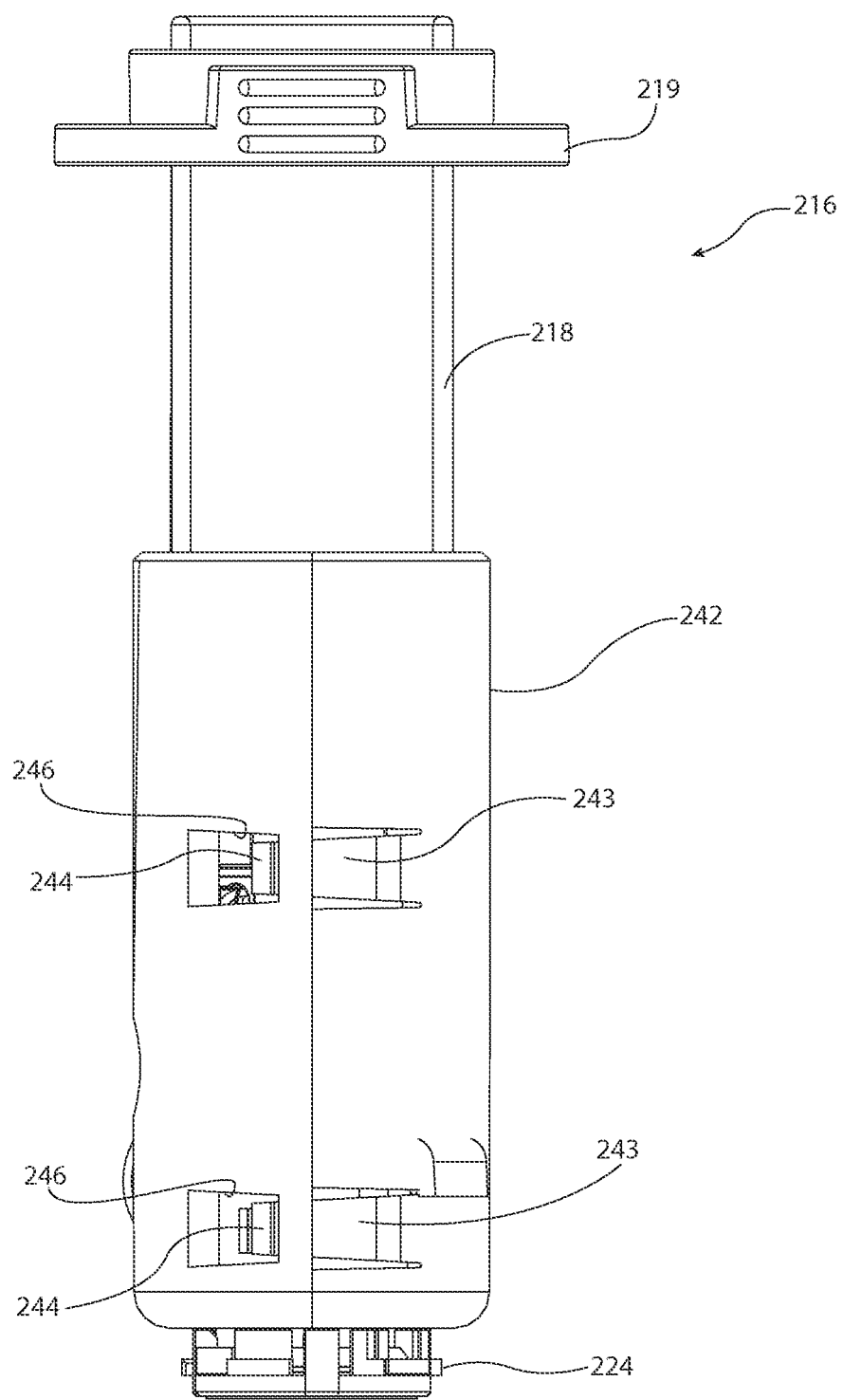
FIG. 9 is a side elevational view of another embodiment of a fill-finish cartridge, wherein the cartridge includes a fully disposable carrier.
Figure 10:
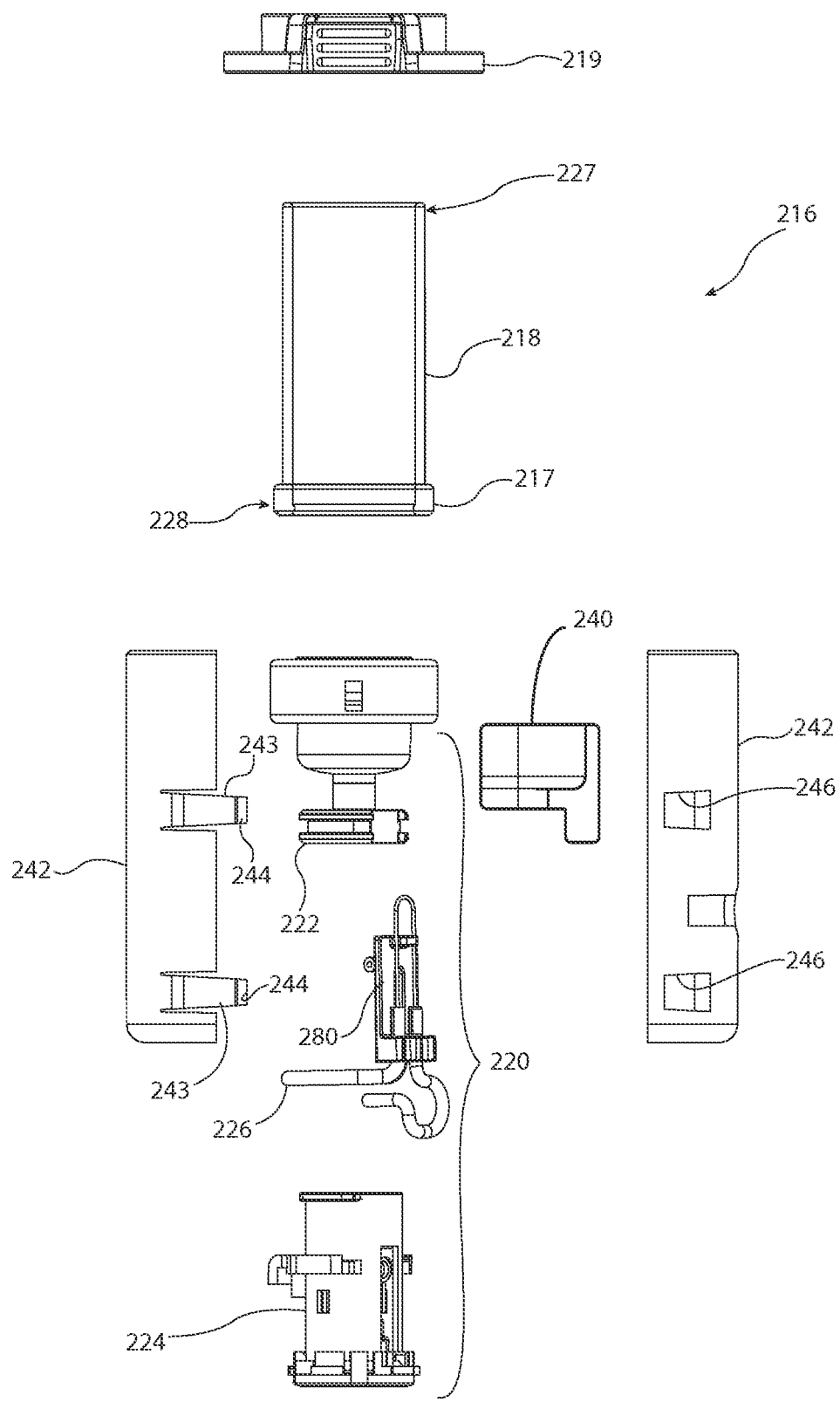
FIG. 10 is an exploded view of the fill-finish cartridge of FIG. 9.
Figure 11:
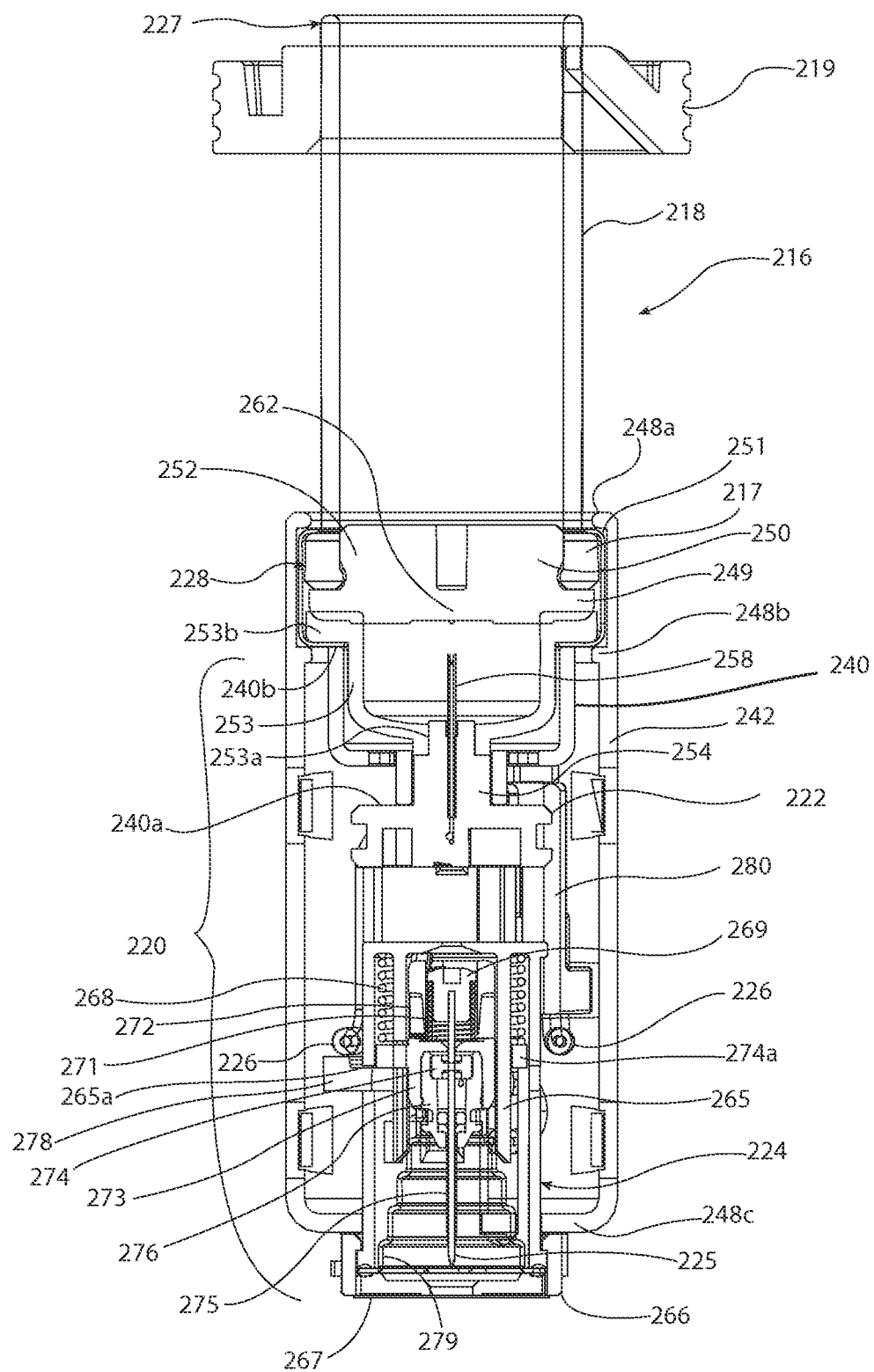
FIG. 11 is a cross-sectional view of the fill-finish cartridge of FIGS. 9 and 10, cross-hatching being eliminated for the purposes of clarity.
Figure 12:
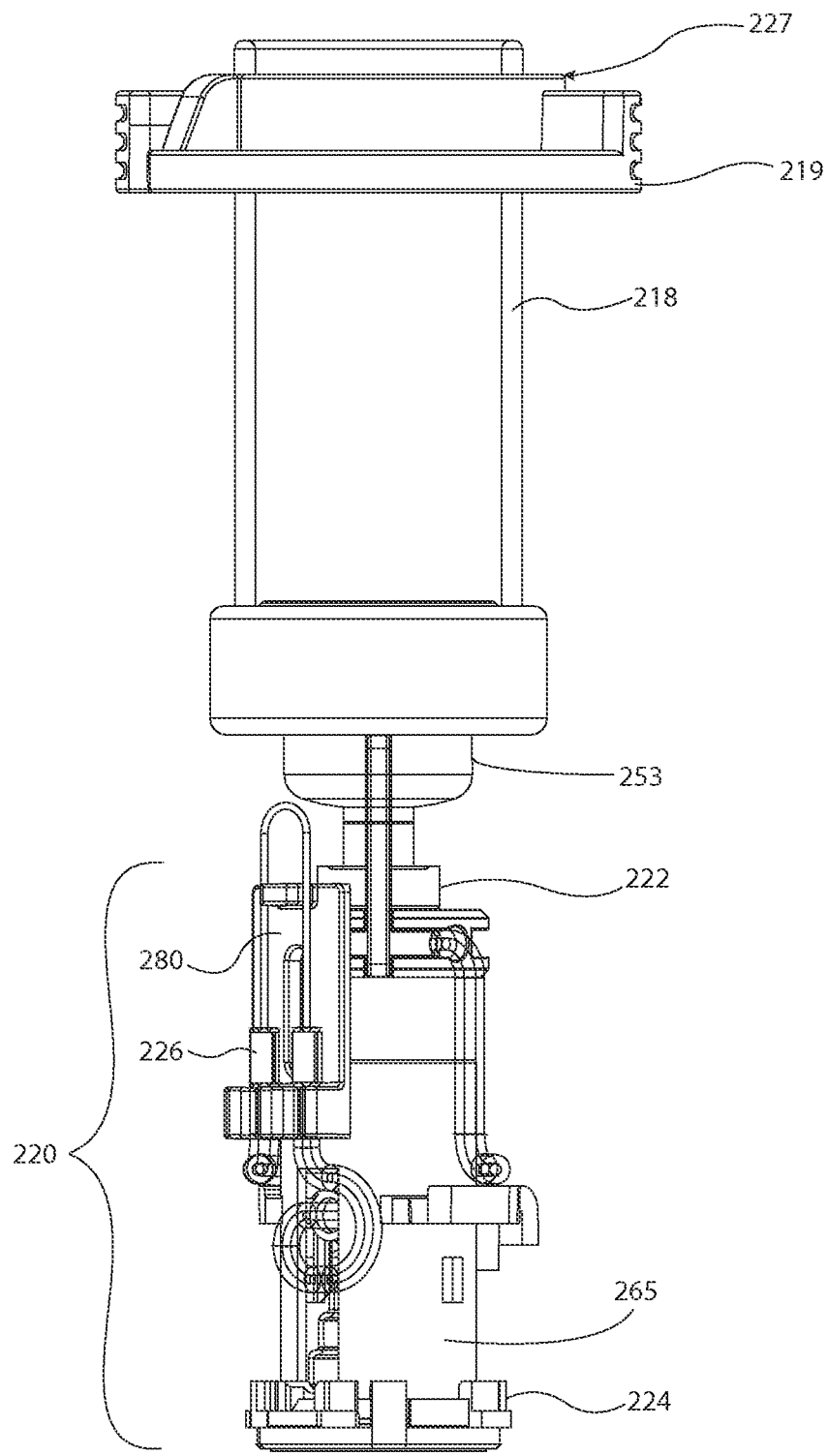
FIG. 12 is a side elevational view of the fill-finish cartridge of FIGS. 9-11 with the carrier removed.

In the embodiment of FIGS. 9-11, there is illustrated a fill-finish cartridge 216 that includes a carrier 242 that may be disposed of after the fill-finish process, that is prior to insertion into a drug delivery device. The fill-finish cartridge 216 of this embodiment includes a fluid pathway assembly 220 connected to a drug container 218. The fluid pathway assembly 220 includes a needle insertion mechanism 224 coupled to a fluid pathway connection 222 by a fluid conduit 226. A proximal end of the needle insertion mechanism 224 is connected to a distal end of a fluid conduit 226, which is connected at its proximal end to the fluid pathway connection 222. In order to provide further support to the fill-finish cartridge 216, the illustrated carrier 242 is disposed about portions of the drug container 218 and the fluid pathway assembly 220, that is, the fluid pathway connection 222, the fluid conduit 226, and a portion of the needle insertion mechanism 224.

The carrier 242 is generally an elongated tubular structure that may be fabricated in multiple components to facilitate assembly and disassembly, if desired. In the illustrated embodiment, one portion of the carrier 242 includes circumferentially extending arms 243 having protrusions 244, while a mating portion of the carrier 242 includes recesses or openings 246 through which the protrusions 244 may extend when assembled about the fill-finish cartridge 216.

In order to assist in maintaining the components of the fill-finish cartridge 216 in their relative positions, the carrier 242 may further include one or more radially projecting flanges 248a, 248b, 248c. As will be apparent from the explanation below, flanges 248a and 248b may be disposed to further secure aspects of the fluid pathway connection 222 and the drug container 218 in their relative positions. Further, as will likewise be apparent from the explanation below, flanges 248b and 248c may be disposed to maintain the fill-finish cartridge 216 in an unactuated position during filling, and, optionally, placement within a drug delivery device. In order to permit actuation of the device, the carrier 242 may be removed from the fill-finish cartridge 216 and discarded. The carrier 242 may further include a removable brace 240. The removable brace 240 may have a generally U-shaped structure and surfaces that confront the surfaces of the fill-finish cartridge 216 to prevent premature completion of the fluid pathway from the drug container 218 to the fluid pathway connection 222. The removable brace 240 may remain with the fill-finish cartridge 216 as it is assembled into a housing of a drug delivery device; in some embodiments, structure within the housing of the drug delivery device may confront one or more surfaces of the removable brace 240 to cause the removable brace 240 to disengage from the fill-finish cartridge 216 as it is assembled into the housing.

The drug container 218 is an elongated, generally annular structure, although the drug container 218 may be of an alternate design. For example, a flange 219 may be provided at any appropriate location along the drug container 218. Such a flange 219 may be integrally formed with the drug container 218 or may be a separate element that is secured to the drug container 218. In the illustrated embodiment, the flange 219 is a separate component that is coupled to a proximal end 227 of the drug container 218. In an embodiment, the flange 219 may interface with a wall of a housing of a drug delivery device incorporating the fill-finish cartridge 216. Further, in this embodiment, a flange 217 is provided at the distal end 228 of the drug container 218. As illustrated in FIG. 11, the flange 217 may engage with flange 248a of the carrier 242 to facilitate the maintenance of the relative positions of the components of the fill-finish cartridge 216 during the fill-finish process and handling.

In order to seal the drug container 218, a permeable seal 250 may be provided at the distal end 228 of the drug container 218. In this way, a drug contained within the drug container 218 may be maintained in a sterile environment until such time as the seal 250 is pierced by the fluid pathway connection 222 to complete the fluid pathway. The drug container 218 may be assembled with the permeable seal 250 and the fluid pathway assembly 220 for sterilization prior to or after fill. The permeable seal 250 may be of any appropriate design and material. The permeable seal 250 includes a thin membrane 262 or the like that may be pierced in order to complete the fluid pathway from the drug container 218 through the fluid pathway connection 222 and fluid conduit 226 to the needle insertion assembly 224.

The permeable seal 250 may include structure that facilitates connection with the drug container 218 and/or the fluid pathway connection 222. For example, the permeable seal 250 may include a portion 252 that rests inside the drug container 218, providing a mating surface to mount the permeable seal 250 to the drug container 218.

The fluid pathway connection 222 maybe of any appropriate design. Such piercing arrangements are disclosed, for example, in U.S. application Ser. No. 13/612,203, and in U.S. application Ser. No. 13/796,156, both of which are assigned to the assignee of this application and are incorporated herein by reference.

Referring to FIG. 11, the illustrated fluid pathway connection 222 includes a cannula 258 that is disposed to pierce the membrane 262 of the permeable seal 250 during actuation, the cannula 258 being spaced from the permeable seal 250 in the unactuated position (see FIG. 11), and progressing respectively axially in a proximal direction to confront and pierce the membrane 262 as a result of actuation. In the embodiment shown in FIG. 11, the fluid pathway connection 222 includes a hub 254 through which the cannula 258 extends. A pathway from the cannula 258 secured within the hub 254 extends from the lumen of the cannula 258 to a lumen of the fluid conduit 226. Accordingly, when the cannula 258 pierces the membrane 262 of the permeable seal 250, the fluid pathway is provided between the drug container 218, the fluid conduit 226 and the needle 225 of the needle insertion mechanism 224.

In order to maintain the hub 254 and, therefore, the cannula 258 in a desired position relative to the permeable seal 250 closing the drug container 218, the fluid pathway connection 222 further includes a boot 253 formed of collapsible material, such as an elastomeric material. A distal end of the boot 253 includes a generally axially extending bore 253a that is disposed about a portion of the hub 254, while a proximal end of the boot 253 includes a generally radially extending flange 253b. The permeable seal 250 may also include a flange 249 that may be sandwiched between the flange 253b of the boot 253 of the fluid pathway connection 222 and the flange 217 at the distal end 228 of the drug container 218. As with the embodiment illustrated in FIGS. 3-6, a retaining structure, such as a cap 251 may be provided about the periphery of the flanges 217, 249, 253b.

The fluid pathway connection 222 of the fill-finish cartridge 216 may be caused to pierce the membrane 262 of the permeable seal 250 to complete the fluid pathway, for example, by manual depression of the proximal end 227 of the drug container 218 or by an alternate arrangement. During actuation, the boot 253 bows outward to allow relative axial movement between the hub 254 and the permeable seal 250 such that the cannula 258 pierces the membrane 262 of the permeable seal 250 to fluidly connect the drug container 218 to the delivery needle 225 of the needle insertion mechanism 224 via the fluid conduit 226.

In order to inhibit inadvertent activation of the fluid pathway connection 222 once the carrier 242 is removed, the removable brace 240 may be provided about a portion of the circumference of the sterile boot 253 and/or between surfaces that inhibit axial movement of the hub 254 relative to the drug container 218. The removable brace 240 may be a relatively rigid structure that confronts opposing surfaces 240a, 240b, for example, on a surface of the hub 254, and the flange 253b of the sterile boot 253 or, as here the cap 251 along the flange 253b; as a result, the removable brace 240 inhibits axial movement of hub 254 relative to the seal 250. The removable brace 240 illustrated also closely follows at least a portion of the periphery of the sterile boot 253; as a result, the removable brace 240 likewise prevents the sterile boot 253 from bowing outward as the cannula 258 moves axially to pierce the seal 250. In this embodiment, the removable brace 240 may be slid out of position on the sterile boot 253 by the user prior to assembling the fill-finish cartridge 216 into the drug delivery device or by the action of placement into the drug delivery device, for example, as the removable brace 240 engages confronting surfaces of the housing of the delivery device (not illustrated).

The needle insertion mechanism 224 may be of any appropriate design. The needle insertion mechanism 224 illustrated in connection with the embodiment of FIGS. 9-12 likewise includes a needle retraction mechanism, and is shown and explained in greater detail in U.S. application Ser. No. 13/599,727, which is incorporated by reference.

The insertion mechanism 224 includes an insertion mechanism housing 265 having one or more lockout windows 265a, a base 266, and a sterile boot 279. The base 266 includes an opening to passage of the needle 225 and may include a sealing membrane 267 that, at least in one embodiment, is removable prior to use of the fill-finish cartridge 216. Alternatively, the sealing membrane 267 may remain attached to the bottom of the base 266 such that the needle 225 pierces the sealing membrane 267 during operation of the fill-finish cartridge 216 within the drug delivery device incorporating the same.

The insertion mechanism 224 may further include an insertion biasing member 268, a hub 269, a needle 225, a refraction biasing member 271, a clip 272, a manifold guide 273, a septum 274, a cannula 275, and a manifold 276. As illustrated in FIG. 11, both the insertion and retraction biasing members 268, 271 are held in energized states. The manifold 276 may connect to sterile fluid conduit 226 to permit fluid flow through the manifold 276, cannula 275, and into the body of the user during drug delivery, as will be described in further detail herein.

As used herein, "needle 225" is intended to refer to a variety of needles including but not limited to conventional hollow needles, such as a rigid hollow steel needles, and solid core needles often referred to as "trocars." In an embodiment, the needle 225 may be a 27 gauge solid core trocar and in other embodiments, the needle may be any size needle suitable to insert the cannula for the type of drug and drug administration (e.g., subcutaneous, intramuscular, intradermal, etc.) intended.

Upon assembly, the proximal end of needle 225 is maintained in fixed contact with hub 269. The needle 225 may be positioned to move through a cannula 275, if provided, in order to further control movement of the needle 225. The hub 269, and therefore the needle 225, is maintained in selective contact with the manifold guide 273 by the clip 272. While biasing members 268 and 271 bear on the manifold guide 273, the manifold guide 273 is maintained in position by at least one lockout pin 278, which extends through window 265a of the housing 265.

Actuation of the needle insertion 224 device results from removal of the lockout pin 278. The lockout pin 278 may be removed from the window 265a either directly or indirectly as a result of actuation of the fill-finish cartridge 216. Upon removal of the lockout pin 278, the manifold guide 273 carrying the hub 269 and needle 225 is permitted to move axially under the biasing force of the injection biasing member 268. That is, the needle 225 moves into the injection position. As the hub 269 and needle 225 move to the injection position, the sterile boot 279 collapses.

In at least some embodiments, such as the embodiment shown in FIG. 11, the needle insertion mechanism 224 further includes a refraction mechanism that retracts the needle 225 following injection. Such a retraction mechanism may be of any appropriate design. As the manifold guide 273 moves axially in the distal direction, the clip 272 releases the hub 269. Upon release, the biasing force of the retraction biasing member 271 causes hub 269 and the associated needle 225 to retract.

As with the embodiment of FIGS. 3-6, the needle insertion mechanism 224 of FIGS. 9-12 includes an axially aligned structure, such that the administration needle 225 extends axially from a distal end of the fill-finish cartridge 216 during administration. It will be appreciated that the components may be secured together by any appropriate structure and method. The relative positions of the fluid pathway connection 222 and the needle insertion mechanism 224 may be maintained by, for example, a bracket 280, as may be seen in FIGS. 10-12. The illustrated bracket 280 extends between the hub 254 of the fluid pathway connection 222 and the insertion mechanism housing 265, as may best be seen in FIG. 11. The bracket 280 may perform additional functions such as, for example, management of the fluid conduit 226.

It will be appreciated that in some embodiments wherein the bracket 280 is removed from its connection with either of the fluid pathway connection 222 or the needle insertion mechanism 224, or wherein the fill-finish cartridge does not include the bracket 280, the fluid conduit 226 may provide a flexible fluid connection between the fluid pathway connection 222 and the needle insertion mechanism 224, allowing the needle insertion mechanism 224 and the fluid pathway connection 222 to be placed other than in axial alignment. Such embodiments are illustrated, for example, in FIG. 1 or FIGS. 13-16.

Figure 13:
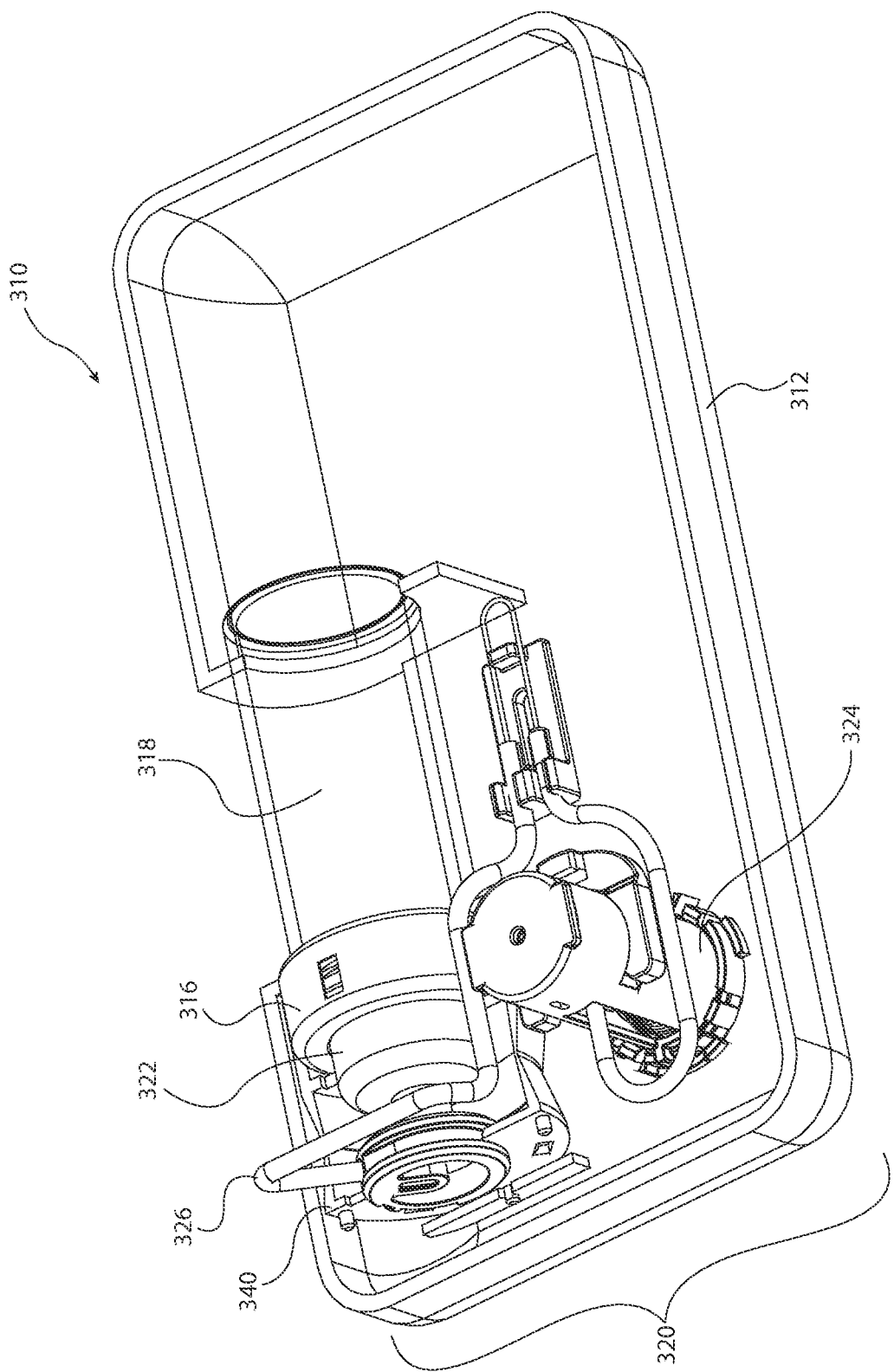
FIG. 13 is an isometric view of a drug delivery device incorporating another embodiment of a fill-finish cartridge according to the invention, a portion of a housing of the drug delivery device being removed.
Figure 14:
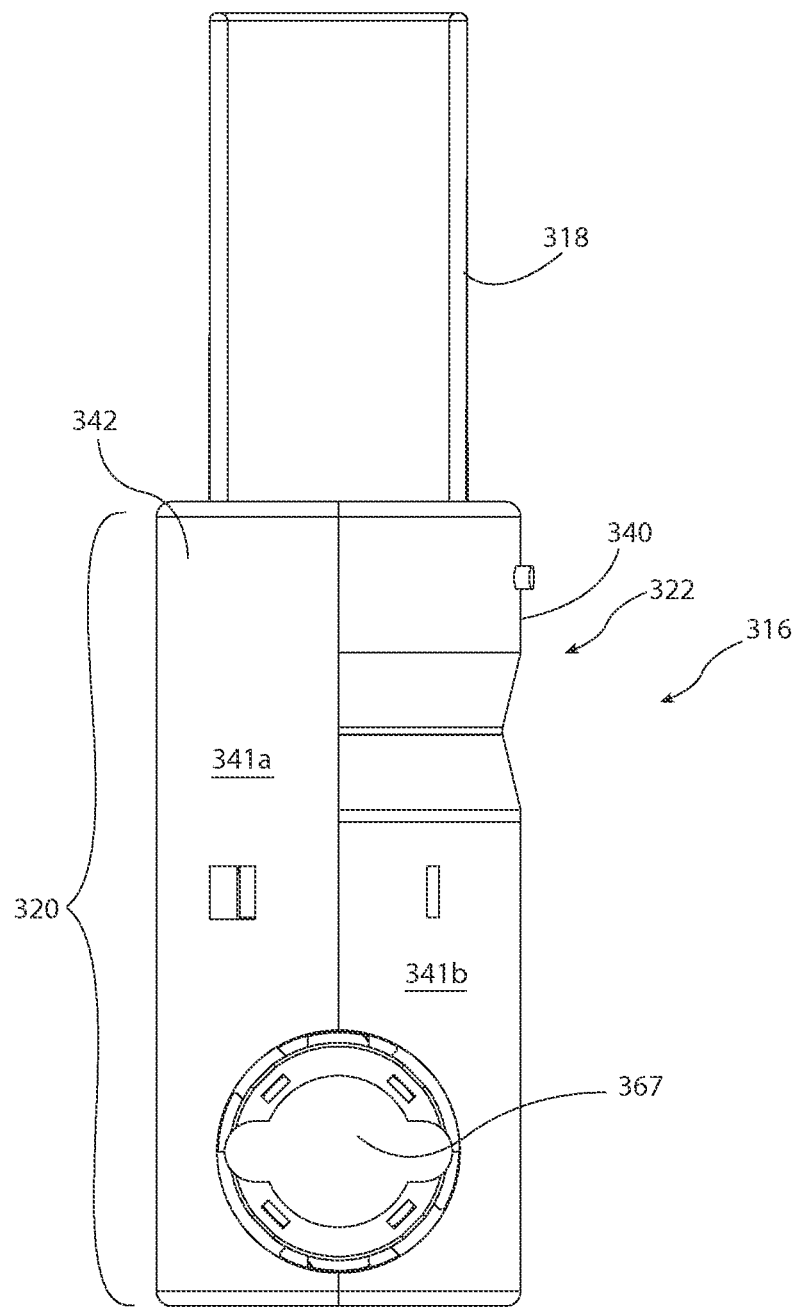
FIG. 14 is a side elevational view of the fill-finish cartridge of FIG. 13 prior to placement in the housing, and including partially disposable carrier.
Figure 15:
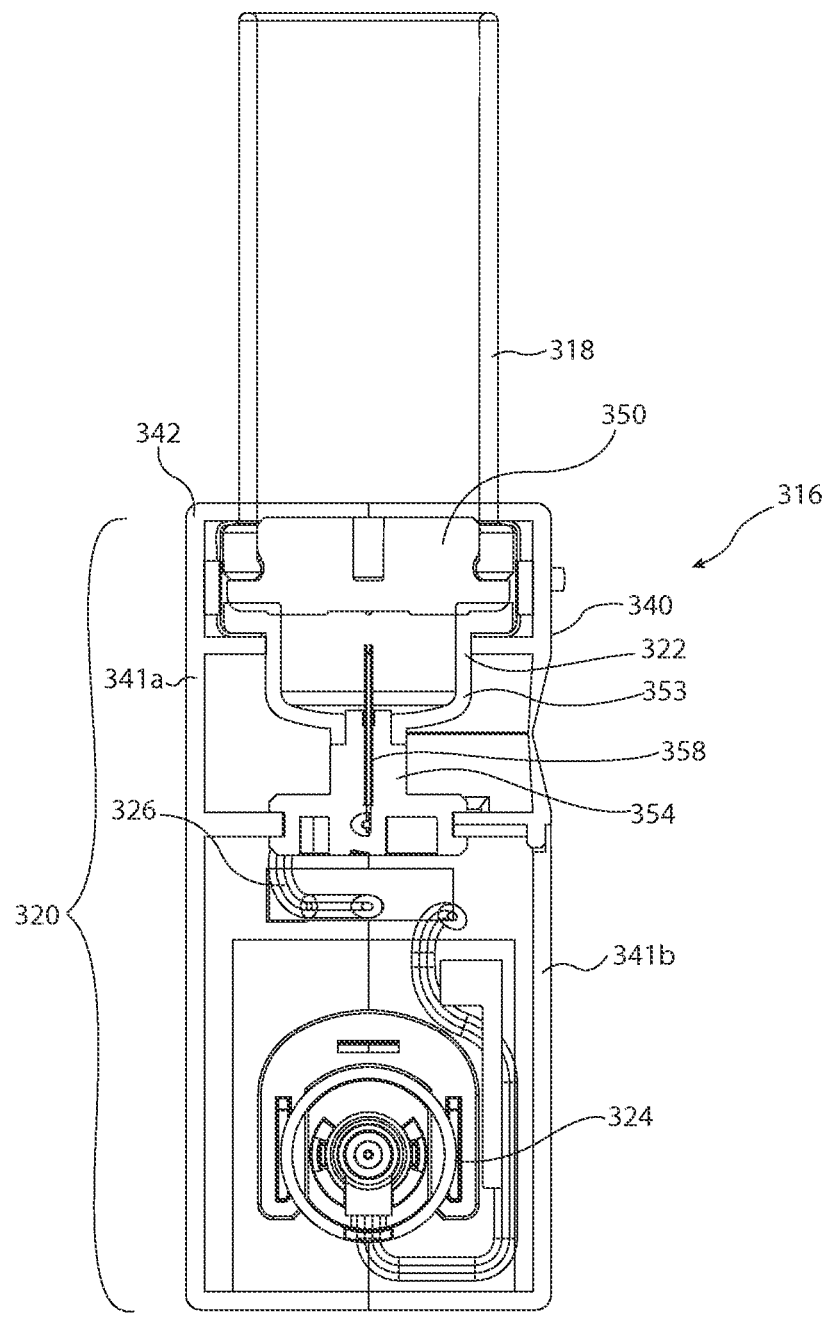
FIG. 15 is a cross-sectional view of the fill-finish cartridge of FIG. 14, cross-hatching being eliminated for the purposes of clarity.
Figure 16:
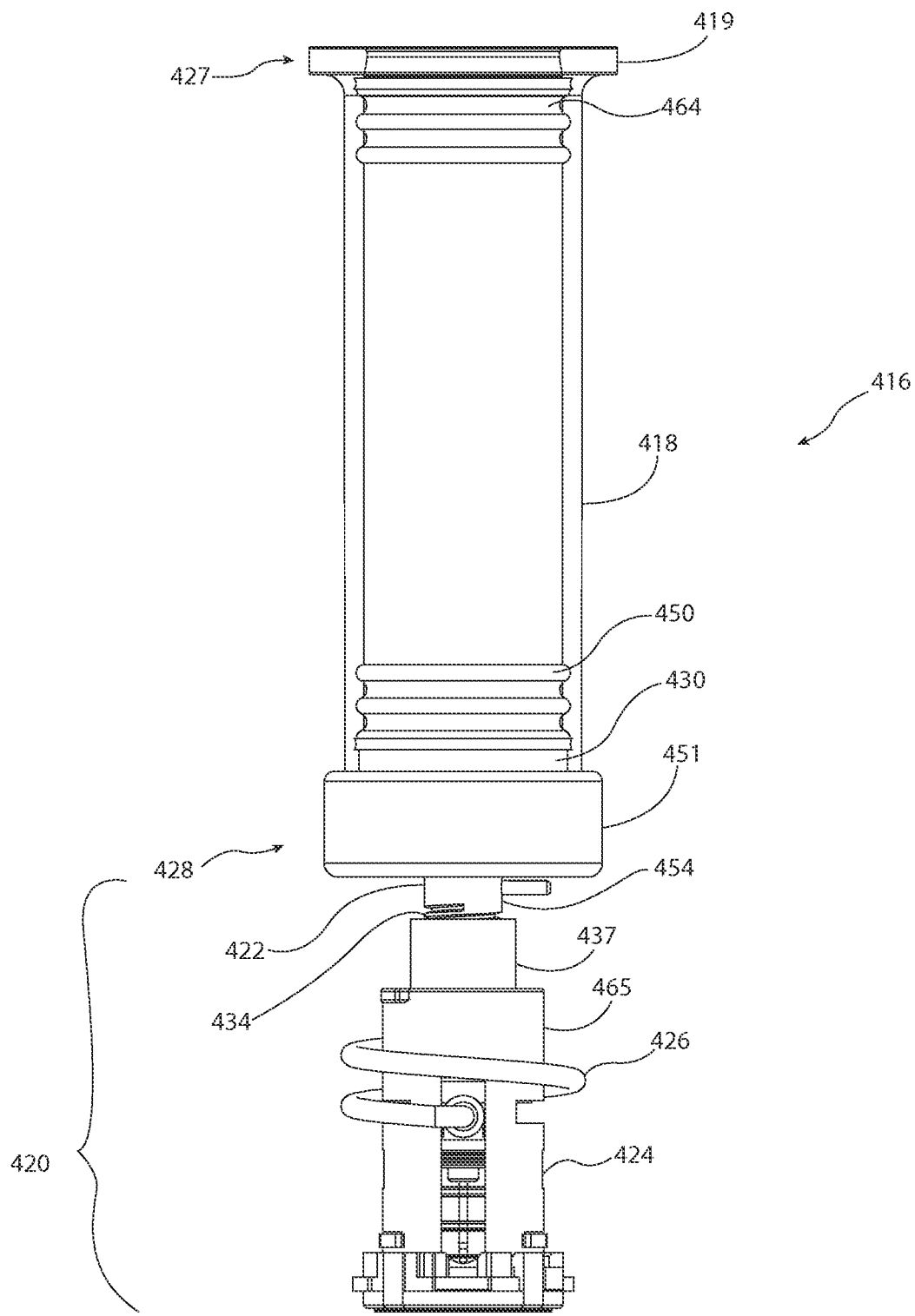
FIG. 16 is a side elevational view of another embodiment of a fill-finish cartridge in an assembled configuration.

Referring to FIG. 13, there is illustrated another embodiment of a drug delivery device 310 according to teachings of the invention. A portion of the housing 312 of the drug delivery device 310 is broken away in order to illustrate the relative positions of the components contained therein. The fill-finish cartridge 316 includes a drug container 318 to which a fluid pathway assembly 320 is coupled. The fluid pathway assembly 320 includes a fluid pathway connection 322, fluidly coupled to a needle insertion mechanism 324 by a fluid conduit 326. It will be appreciated that, in this embodiment, while they remain fluidly coupled, the needle insertion mechanism 324 is decoupled from the fluid pathway connection 322 of the fill-finish cartridge 316 when assembled into the housing 312. As shown in FIGS. 14 and 15, during the fill-finish process, the components are aligned to allow the fill-finish cartridge 316 to be readily placed in a tray, such as are illustrated in FIGS. 7 and 8. It is noted, however, that the components are not in axial alignment in the fill-finish cartridge 316 during the fill-finish process inasmuch as the axis of the needle insertion mechanism 324 extends perpendicular to the axis of the drug container 318 and fluid path connection 322. As may be best seen in FIG. 14, the needle insertion mechanism 324 may include a sealing membrane 367 that, at least in one embodiment, is removable prior to use of the fill-finish cartridge 316 within the drug delivery device to allow passage of a needle from the needle insertion mechanism 324. Alternatively, the sealing membrane 367 may remain attached to the bottom of the needle insertion mechanism 324 such that the needle pierces the sealing membrane 367 during operation of the fill-finish cartridge 316 within the drug delivery device 310 incorporating the same.

Referring to FIG. 14, there is illustrated the fill-finish cartridge 316 along with a carrier 342 that partially surrounds the assembled fill-finish cartridge 316 during the fill-finish process. As may be seen in FIG. 14, the carrier 342 substantially surrounds a distal portion of the drug container 318, the fluid pathway connection 322, and the needle insertion mechanism 324. The carrier 342 of this embodiment includes three separate sections, although a greater or lesser number may be provided. In this embodiment, a portion of the carrier 342 is disposable prior to placement of the fill-finish cartridge 316 into the housing 312 of the drug delivery device 310, while a portion remains on the fill-finish cartridge 316 when disposed in the housing 312, and may be utilized in operation of the device 310.

As may be seen in FIGS. 14 and 15, the carrier 342 includes a first barrel section 341a and a second barrel section 341b. The first and second barrel sections 341a, 341b may be selectively coupled together by any appropriate mechanism. In the illustrated embodiment, a coupling arrangement similar to that illustrated in FIGS. 9-11 is utilized such that the first and second sections 341a, 341b may be decoupled and removed prior to placement into the housing 312 of the drug delivery device 310. The carrier 342 further includes a collar 340 that, when assembled to the fill-finish cartridge 316, completes the barrel.

The fluid pathway connection 322 and the needle insertion mechanism 324 may be of any appropriate design. The illustrated fluid pathway connection 322, for example, is as explained with regard to FIGS. 9-11, and the needle insertion mechanism 324 may likewise be as described with regard to FIGS. 9-12. Referring to FIG. 15, in short, a permeable seal 350 is disposed between the drug container 318 and a sterile boot 353 of the fluid pathway connection 322. A cannula 358 extending from a hub 354 is axially disposed within the sterile boot 353. Continued relative axial, proximal movement of the cannula 358 toward the permeable seal 350 results in a piercing of the permeable seal 350, and completion of the fluid pathway to the needle insertion mechanism 324.

In assembly of the filled fill-finish cartridge 316 into the drug delivery device housing 312, the collar 340 remains coupled to the fluid pathway connection 322, as illustrated in FIG. 13. In some embodiments of the invention, the carrier, or a portion of the same such as the collar 340 here, may be utilized in the operation or actuation of the fill-finish cartridge 316. In this embodiment, an activation mechanism 314, such as a button, may be provided along an outer surface of the drug delivery device housing 312 in order to permit the user to selectively provide medication. In this embodiment, the activation mechanism 314 asserts an axial, proximally directed force on the collar 340. The collar 340 further asserts an axial, proximally directed force on the hub 354, causing the cannula 358 to pierce the permeable seal 350 of the fluid pathway connection 322 to complete the fluid pathway from the drug container 318 to the needle insertion mechanism 324. The needle insertion mechanism 324 may be actuated by any appropriate operation. For example, the movement of a portion of the collar 340 may cause the dislodgement of the lockout pin, causing actuation of the needle insertion mechanism 324, as explained in greater detail with regard to the embodiment illustrated in FIGS. 9-12.

Turning now to the embodiment of FIGS. 16-22, the fill-finish cartridge 416 includes a drug container 418 having proximal and distal ends 427, 428. The proximal end 427 may include a flange 419 and is adapted to receive a plug or plunger seal 464, while the distal end 428 may include a flange 417 and is adapted to receive a permeable seal 450 in conjunction with a fluid pathway assembly 420. The fluid pathway assembly 420 includes a fluid pathway connection 422 and a needle insertion mechanism 224 fluidly coupled by a fluid conduit 426.

In this embodiment, the fluid pathway connection 422 is integrated with the permeable seal of the drug container 418. The fluid pathway connection 422 may best be seen in the cross-sectional view of FIG. 17 and the exploded view of FIG. 19. The fluid pathway connection 422 includes a hub assembly 456 having a hub 454 and a cap 455. A cannula 458 is secured to the hub 454 to provide a fluid path therethrough. The fluid conduit 426 may be coupled to the cannula 458 by any appropriate structure. In this embodiment, the fluid conduit 426 is coupled to a nipple 459 that is fluidly open to the cannula 458.

In order to maintain the hub assembly 456 along with the associated cannula 458 in position relative to the permeable seal 450, a seal mount 430 is provided. While the seal mount 430 may be coupled to the permeable seal 450 by any appropriate structure, in the illustrated embodiment, the permeable seal 450 and the seal mount 430 include mating structure in the form of respective interlocking flanges 431, 432.

Figure 17:
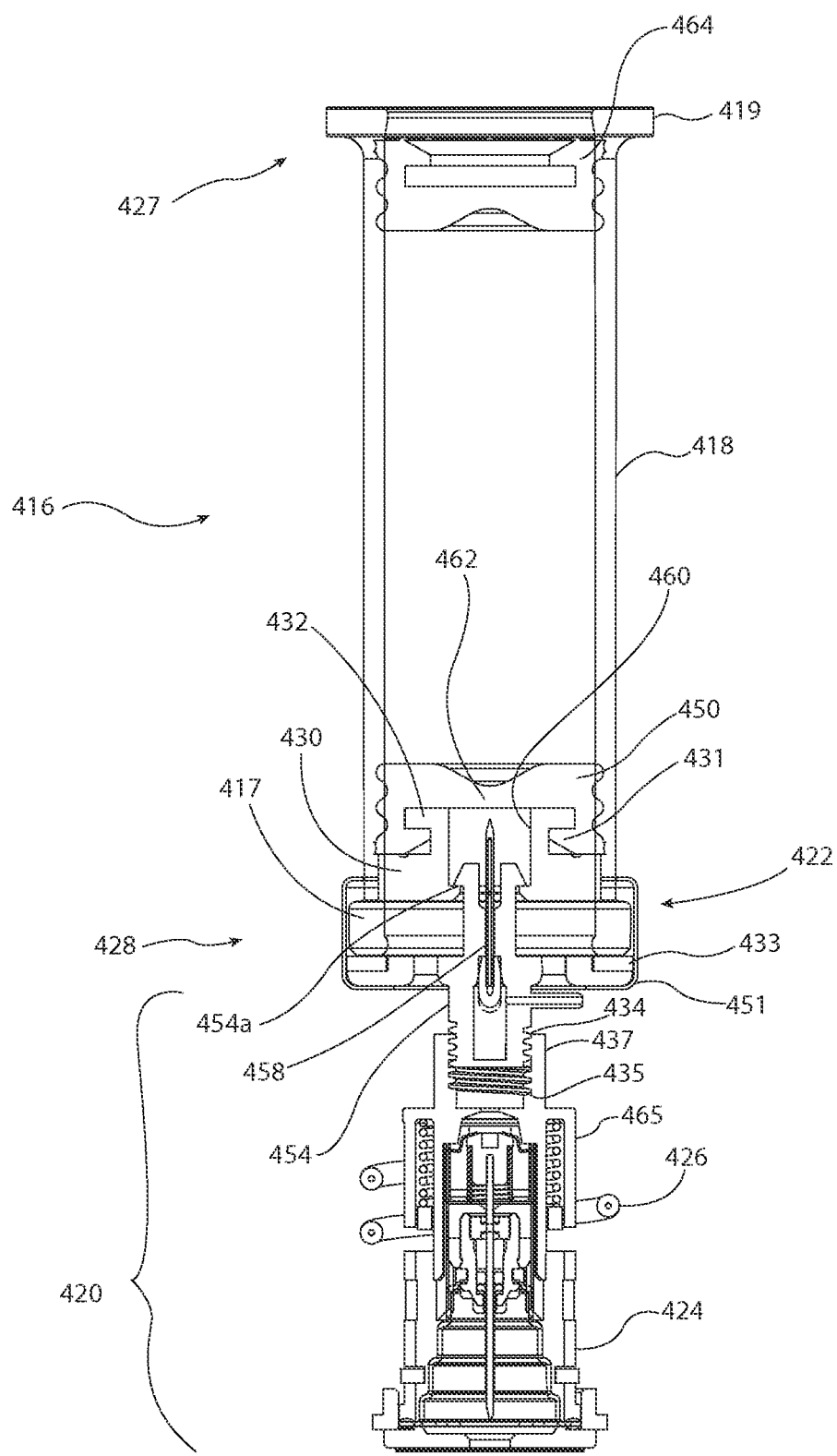
FIG. 17 is a cross-sectional view of the fill-finish cartridge of FIG. 16, cross-hatching being eliminated for the purposes of clarity.
Figure 18:
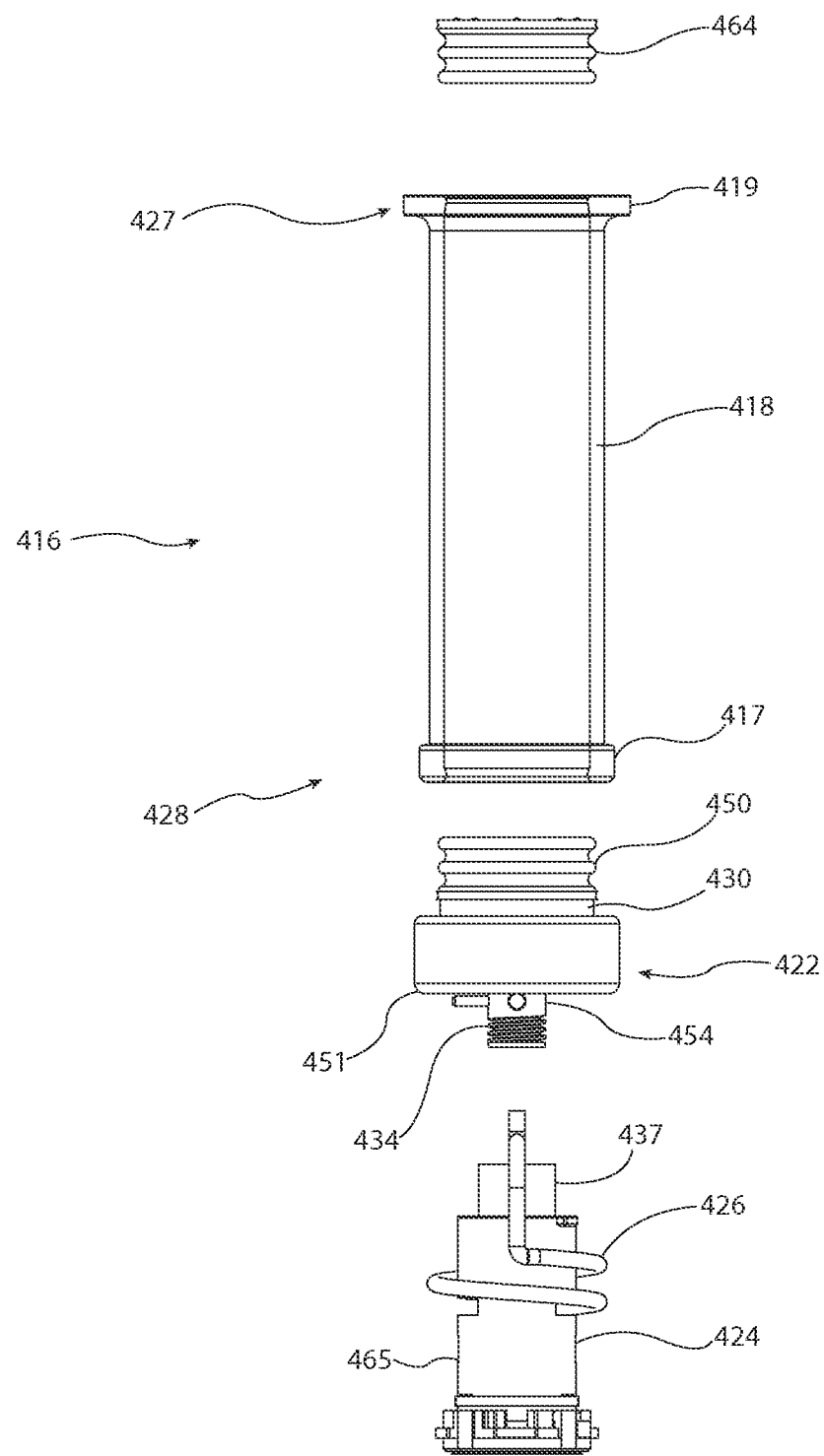
FIG. 18 is a partially exploded view of the fill-finish cartridge of FIGS. 16 and 17, showing a fluid conduit in the final configuration.
Figure 19:
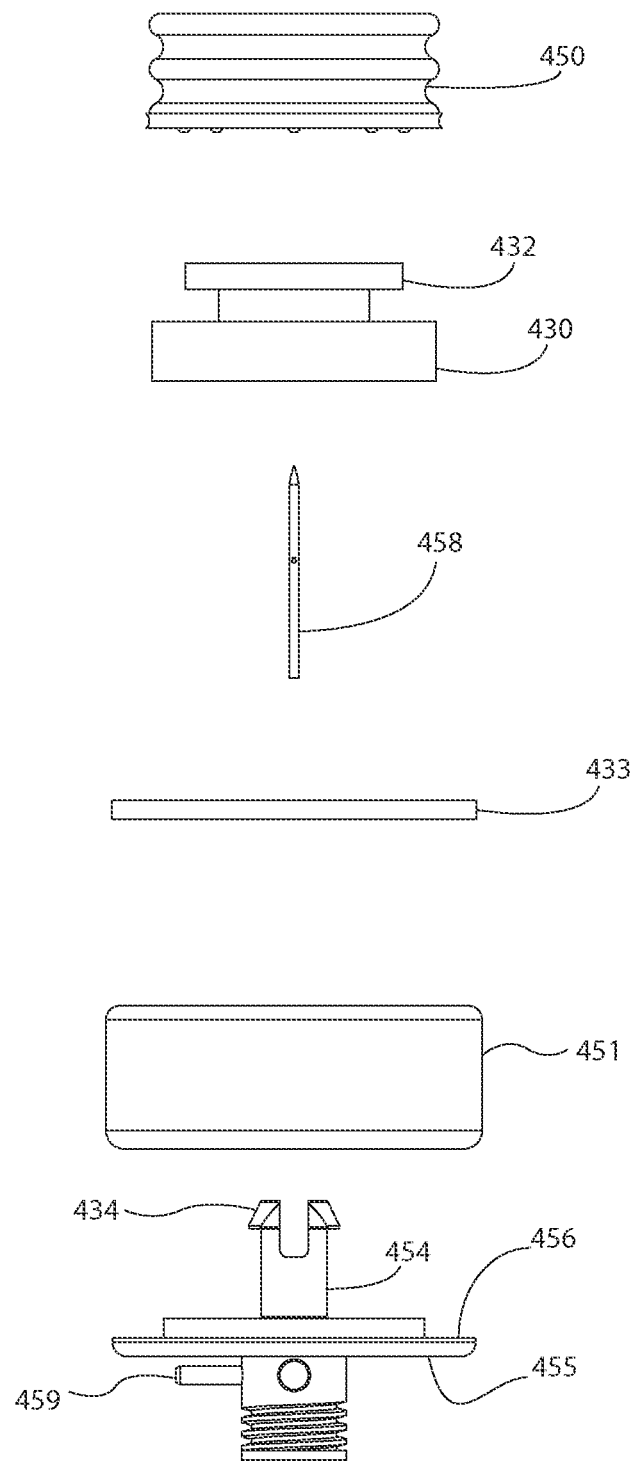
FIG. 19 is an exploded view of the fluid pathway connection of the fill-finish cartridge of FIGS. 16-18.

While the hub assembly 456 may be assembled with the seal mount 430 and permeable seal 450 for coupling to the drug container 418, the permeable seal 450 and seal mount 430 are slidably disposed relative to the hub assembly 456. In order to allow this sliding, yet coupled relationship, the hub 454 includes one or more resilient posts 454a that present surfaces that interlock with a complimentarily disposed bore 460 in the seal mount 430. As shown in FIG. 17, the when assembled together, the cannula 458 is disposed subjacent the membrane 462 of the permeable seal 450. In this way, the permeable seal 450, the seal mount 430 and the coupled hub assembly 456 form an integrated fluid pathway connection 422 that may be assembled into the distal end 428 of the container 418.

In order to further facilitate assembly of the fluid pathway connection 422 to the container 418, a cap 451 may be provided. One or more gaskets 433 may be provided between adjacent surfaces of the fluid pathway connection 422 and, for example, the flange 417 of the drug container 418. One such gasket 433 is illustrated in FIG. 17, although additional gaskets may be provided.

The needle insertion mechanism 424 may be of any appropriate design, such as, for example, the needle insertion mechanism 424 illustrated in FIG. 11. The cannula 458 of the fluid pathway connection 422 is fluidly connected to the needle 425 of the needle insertion mechanism 424 by way of the fluid conduit 426.

In this embodiment the fluid pathway connection 422 and the needle insertion mechanism 424 are coupled, for example by mechanical coupling, by way of complimentary threads 434, 435. In the illustrated embodiment, fluid pathway connection 422, here, the hub 454, includes external threads 434, while the needle insertion mechanism 424, here, a bore 436 of an extension 437 of the insertion mechanism housing 465, includes complimentary internal threads 435. It will be appreciated that alternate arrangements are envisioned. For example, the threading arrangement could be reversed, the fluid pathway connection 422 including internal threads and the needle insertion mechanism 424 including external threads. Alternately, a threaded collar, or the like, could be provided to couple the components together.

Moreover, although the fluid pathway connection 422 and the needle insertion mechanism 424 are coupled in axial alignment in the fill-finish cartridge 416 for the fill process, the components could be alternately disposed. For example, the axis of the needle insertion mechanism 424 could be disposed at a right angle to the axis of the fluid pathway connection 422 and the drug container 418.

Figure 20:
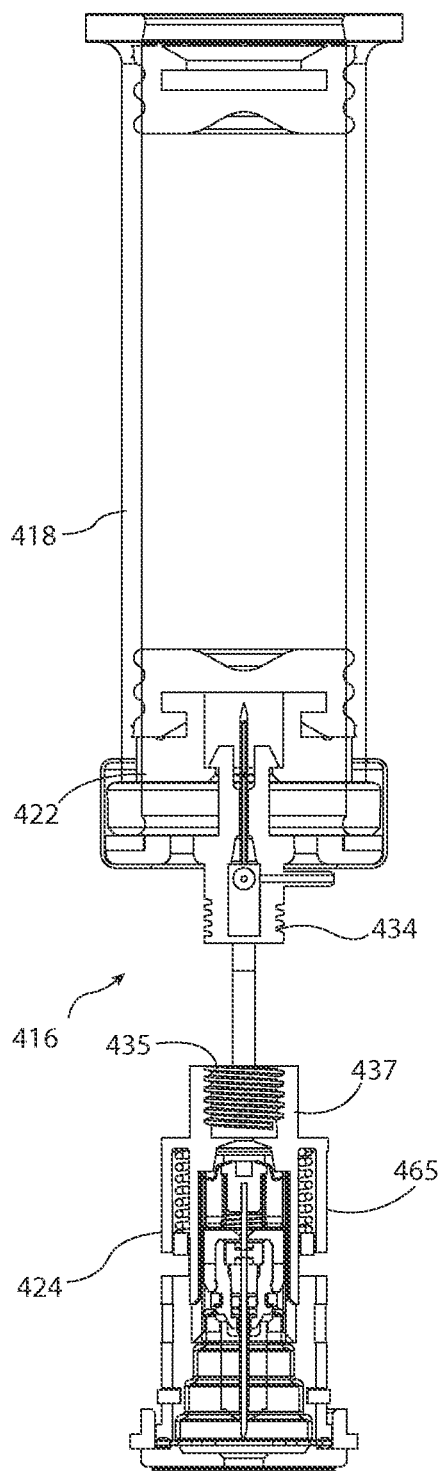
FIG. 20 is a cross-sectional view of the fill-finish cartridge of FIG. 16 similar to the view of FIG. 17, but prior to the coupling of the fluid pathway connection to the needle insertion mechanism, cross-hatching being eliminated for the purposes of clarity.

According to another aspect of the invention, the fill-finish cartridge 416 provides controlled management of the fluid conduit 426. In this embodiment, the threaded coupling of the needle insertion mechanism 424 and the fluid pathway connection 422 may provide controlled placement of the fluid conduit 426. The uncoupled needle insertion mechanism 424 and fluid pathway connection 422 are illustrated in FIG. 20. As the needle insertion mechanism 424 and the fluid pathway connection 422 are threaded together to the positions illustrated in FIGS. 16 and 17, the fluid conduit 426 winds about the housing 465 of the needle insertion mechanism 424. While the needle insertion mechanism 424 and the fluid pathway connection 422 are illustrated in a disassembled configuration with the fluid pathway connection 422 being assembled to the container 418 in FIG. 20, it will be appreciated that the components may be assembled in any order. For example, the needle insertion mechanism 424 and the fluid pathway connection 422 may be assembled together prior to coupling the fluid pathway connection 422 to the container 418 to form the fill-finish cartridge 416.

Figure 21:
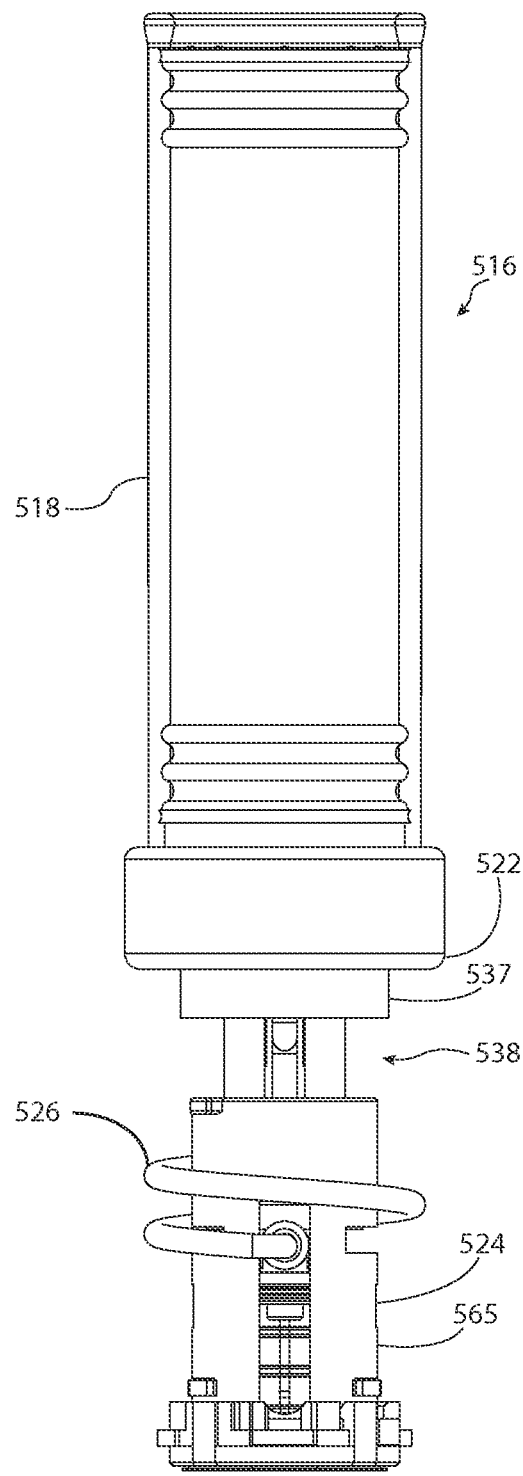
FIG. 21 is a side elevational view of another embodiment of a fill-finish cartridge in an assembled configuration.
Figure 22:
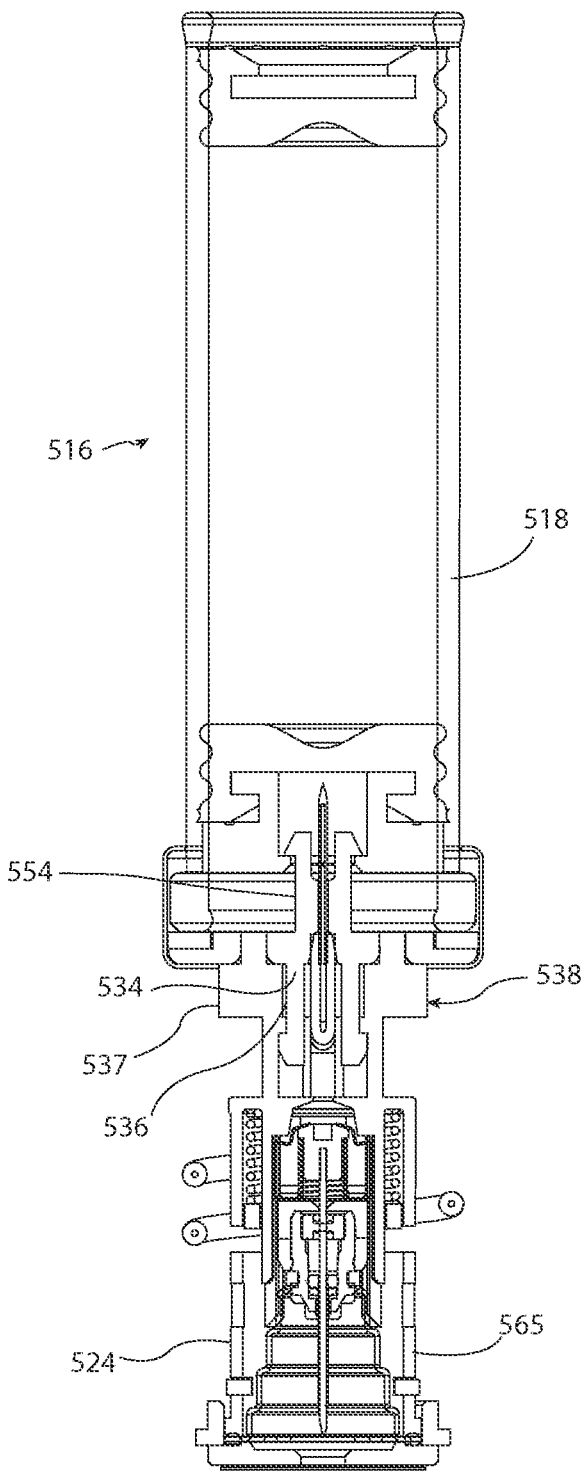
FIG. 22 is a cross-sectional view of the fill-finish cartridge of FIG. 21, cross-hatching being eliminated for the purposes of clarity.
Figure 23:
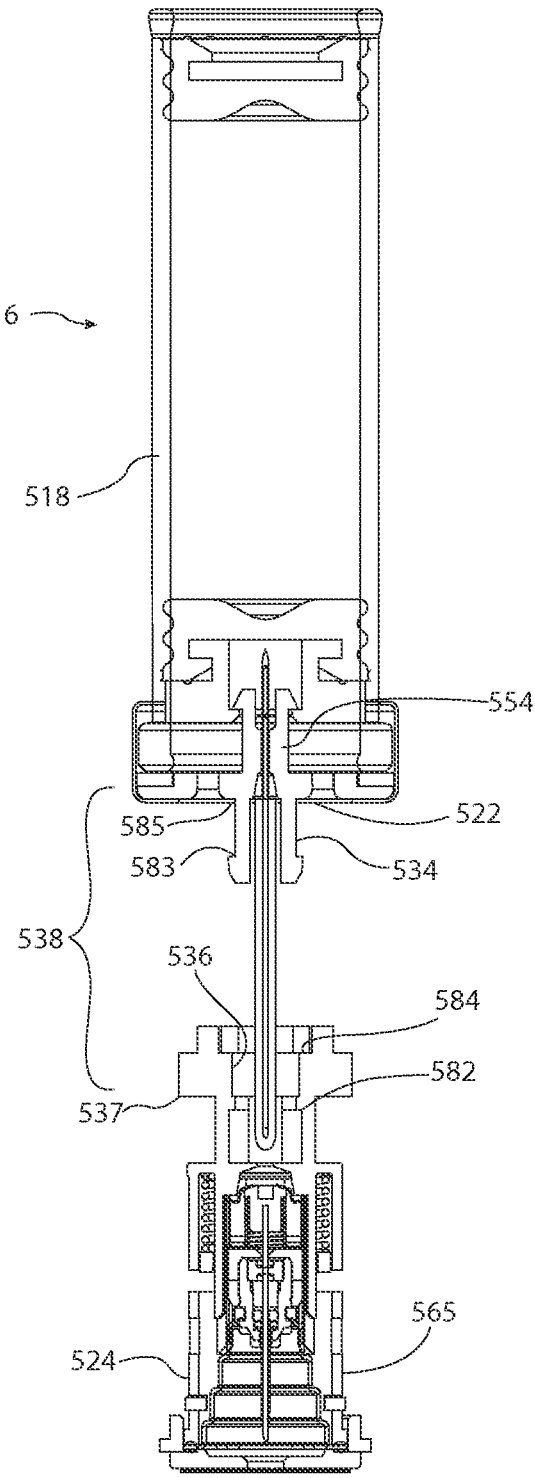
FIG. 23 is a cross-sectional view of the fill-finish cartridge of FIG. 21 similar to the view of FIG. 22, but prior to the coupling of the fluid pathway connection to the needle insertion mechanism, cross-hatching being eliminated for the purposes of clarity.

Turning to the embodiment illustrated in FIGS. 21-23, the fill-finish cartridge 516 illustrated is similar in operation to the fill-finish cartridge 416 of FIGS. 16-20. The fill-finish cartridge 516 of FIGS. 21-23 differs, however, in that the fluid pathway connection 522 is coupled to the needle insertion mechanism 524 by way of a snap connection 538, the needle insertion mechanism 524 and the fluid pathway connection 522 including complementary structure that allow the components to snap together. For example, the housing 565 of the needle insertion mechanism 524 may include an extension 537 having a recess or bore 536, or female portion, adapted to receive a corresponding male portion 534 of the fluid pathway connection 522. In order to ensure axial alignment of the extension 537 and male portion 534, each may present one or more confronting shoulders. For example, the recess 536 of the may include shoulders 582, 584 against which one or more outwardly extending shoulders 583, 585 of the fluid pathway connection 522 seat. To facilitate connection, the hub 554 of the fluid pathway connection 522 may include one or more resilient fingers 586 extending from the hub 554. During assembly, the fingers 586 may flex such that the shoulders 583 may move generally radially inward as the fingers 586 are moved through the recess or bore 536, and snap outward into engagement with shoulders 582 when the fluid pathway connection 522 and the needle insertion mechanism 524 are in their final assembled axial positions. It will be appreciated, however, that the snap connection 538 may have alternate structure as, for example if the fluid pathway connection 522 included a shouldered recess and the needle insertion mechanism 524 included mating outwardly extending shoulders.

As with the embodiment of FIGS. 16-20, the embodiment of FIGS. 21-23 allows for controlled management of fluid conduit 526 fluidly connecting the fluid pathway connection 522 and the needle insertion mechanism 524. For example, the conduit may be wound around the periphery of the housing 565 of needle insertion mechanism 524, as illustrated in FIG. 23, before, after, or during the engagement of the snap connection 538.

While a threaded connection has been described with regard to FIGS. 16-20, and a snap connection with regard to FIGS. 21-23, it will be appreciated that alternate mechanical connections may be utilized to provide sufficient structural integrity to the cartridge to facilitate filling the container in a conventional fill-finish process. For example, a tongue and groove type connection may be utilized. Alternately, or additionally, an external support, such as the bracket 280 of FIGS. 9-12 may be utilized, or the relative positions may be maintained by way of a carrier, such as the carrier 142 of FIGS. 3-6. Other mechanical coupling arrangements are likewise within the purview of the invention.

It will thus be appreciated that the inventive arrangement described herein provide varied designs of components that may be assembled in various configurations to provide various designs of fill-finish cartridges that may be sterilized and filled in conventional fill finish processes.

As a further benefit, because the embodiments of the present invention enable the manufacture of pre-filled infusion or injection pumps, these pumps may be configured to be single-use or reusable pumps. For example, the fluid pathway assemblies and/or fill-finish cartridge of the present invention may be configured to be cartridges which can be replaced within reusable pump devices.

Some embodiments of the present invention enable the drug container to be filled in a standard fill-finish process, without the need to expose the drug treatment to the sterilization environment or conditions. Some drug treatments, however, are capable of withstanding the sterilization conditions without degrading, losing efficacy, or the like. Accordingly, in at least one embodiment of the present invention, sterilization of the fluid pathway assembly and/or the fill-finish cartridge may occur after the components have been assembled and the drug container has been filled with a pharmaceutical treatment. This method of manufacturing, filling, and using the novel embodiments of the present invention still may provide the benefit of being adaptable to a standard fill-finish process. Additionally, this method enables drug delivery device manufacturers and fillers the benefit of only needing to sterilize the components of the fluid pathway (i.e., components which may come in contact with the drug fluid). The fill-finish cartridges, fluid pathway assemblies, and individual components of the present invention may be sterilized prior to their integration in a drug delivery device. As such, the other components of the drug delivery device which generally never contact the drug fluid do not need to be sterilized because of the advantages offered by the present invention. Accordingly, the embodiments of the present invention enable more complex geometries and more standard materials, for example, to be employed for the manufacture of advanced drug delivery devices.

The novel configurations of the fluid pathway assemblies and the fill-finish cartridges of the present invention may provide substantial benefits in the marketplace. Embodiments of the present invention can readily be manufactured in a sterile environment, integrated into standard drug filling (e.g., fill-finish) process lines for aseptic filling of pharmaceutical treatments, and utilized for cost-effective assembly into drug delivery devices. Each of these advantages has substantial benefits over existing methodologies.

For example, because the fluid pathway assemblies themselves can be sterilized and maintained in a sterile condition during the filling and device assembly processes, the resulting drug delivery device does not need to be sterilized after assembly (i.e., terminally sterilized). This avoids a number of known challenges faced by existing methodologies for the manufacture of drug delivery devices.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present invention enable the manufacture, assembly, and use of pre-filled drug delivery devices which maintain the sterility of the fluid pathway assembly through the various manufacturing steps.

Additionally, because the drug delivery devices which incorporate the novel embodiments of the present invention do not need to be terminally sterilized, the components of the devices may comprise of other, often less expensive, materials which would not normally withstand the sterilization environment. For example, less expensive plastics may be utilized for certain device components because they do not need to be sterilized after assembly.

In other words, the embodiments of the present invention may allow the manufacturer to sterilize only the components which will be in contact with the drug fluid and/or which are necessary to maintain sterile fluid pathways. These embodiments may also allow the pharmaceutical filler to maintain the sterility of these components during the filling and finishing steps associated with the assembly of the drug delivery devices. Similarly, drug delivery devices which incorporate the fluid pathway assemblies of the present invention may have smaller or more efficient geometries as the device does not have to be configured for sterilization after assembly.

Additionally, the embodiments of the present invention allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present invention enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner than preserves the sterility of the fluid pathway assembly. The fluid pathway assembly can then, after being filled with a pharmaceutical compound, be mated into a drug delivery device without requiring the remainder of the device components to be sterilized. Accordingly, embodiments of the present invention may provide novel components which enable the fluid pathway assemblies to be sterilized, assembled, filling, and incorporated into drug delivery devices in a cost-efficient and streamlined process.

Additionally, the fluid pathway assemblies of the present invention utilize materials that are substantially non-reactive with therapeutic fluids or drugs, and are suitable for use in pharmaceutical grade applications. The novel fluid pathway assemblies and fill-finish cartridges are configured to minimize or eliminate the possibility of contact or interaction between degradable materials, such as certain plastics, with the therapeutic fluids or drugs. The fluid pathway assemblies, with adaptable needle injection and retraction mechanisms, also may provide fluid conduits from the drug container to the patient, through the needle or cannula, which are substantially absent of degradable materials. Such configurations, when integrated into the fill-finish cartridges or drug delivery devices, may provide increased stability and shelf-life parameters to the drug and drug delivery devices. These characteristics are thought to be highly desirable for generally all pharmaceutical treatments, but perhaps especially of value in drug delivery devices for use with biologics and other complex therapies.

One or more embodiments of the present invention may further include certain standard components. For example, the fill-finish cartridge configurations and drug delivery devices of the present invention may include one or more membranes. In at least one embodiment, one or more permeable membranes are employed to seal the drug container and/or to ensure a sterile environment and container integrity within the drug chamber. Similarly, the drug container may include a flange. The flange may be pre-formed along any portion of the container, or may be a separate component that is connected to or affixed to the container. In at least one embodiment, the flange is a removable connected component that is connected at the proximal end of the drug container. The flange may be configured to allow the fill-finish cartridge and drug container to rest within a fill-finish tray, for filling with a pharmaceutical compound within a standard fill-finish process. The position, shape, number, and materials for such components may vary, as would be readily appreciated by a skilled artisan, to meet any number of desired characteristics.

Similarly, while the components of the fill-finish cartridge and the fluid pathway assembly are described herein as separate components, it is within the contemplation of the present invention that certain groups of these components may be combined to form a single component capable of performing the functions of the individual components. In at least one embodiment the needle insertion and needle retraction mechanisms may be one unified component that may provide a dual function. Additionally, as would be appreciated by one having ordinary skill in the art, the components of the devices may be manufactured as individual components or as single components. For example, the flange may be a component that is pre-formed, during the manufacturing process, as a part of the drug container itself. Accordingly, in at least one embodiment, the flange may be a glass flange extension of the container. Furthermore, while the components of the fill-finish cartridge and fluid pathway assembly are described herein as separate components, they may be unified components having multiple functions. The configuration of the components and their assembly may vary based on the assembly process, the device parameters, and other desired characteristics.

Embodiments of the present invention may provide fluid pathway assemblies, fill-finish cartridges, methods of manufacturing such cartridges, and their methods of use. The fill-finish cartridges and fluid pathway assemblies may be utilized in a number of different configurations and may themselves comprise of one or more components. Such modifications are contemplated by and encompassed in the embodiments of the present invention. Other components may similarly be single components, unified components, or multi-purpose components, as described in the embodiments discussed above. Thus, it is intended that the present invention covers the modifications and variations of this invention may provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A fill-finish cartridge, the cartridge comprising:
   a drug container defining a longitudinal axis,
   a needle insertion mechanism including a needle, the needle insertion mechanism being operative to move the needle to an insertion position,
   a fluid pathway connector coupled to the drug container,
   a flexible fluid conduit fluidly coupling the needle insertion mechanism and the fluid pathway connector, and
   a carrier configured to removably couple the fluid pathway connector and the needle insertion mechanism,
   the fluid pathway connector and the needle insertion mechanism being disposed along the longitudinal axis of the drug container when the carrier is engaged with the fluid pathway connector and the needle insertion mechanism,
   the carrier configured to maintain the relative physical positions of the fluid pathway connector, the needle insertion mechanism, and the drug container, when engaged with the fluid pathway connector and the needle insertion mechanism, and
   the fluid pathway connector being selectively actuable to fluidly connect the drug container to the needle insertion mechanism via the flexible fluid conduit whereby the drug container, the fluid pathway connector, the flexible fluid conduit, and the needle insertion mechanism define a sterile fluid flow path,
   wherein the drug container includes an open proximal end and the cartridge is finable in a fill finish process.

2. The cartridge of claim 1 wherein the needle of the needle insertion mechanism is in axial alignment with the longitudinal axis of the drug container when the carrier is engaged with the fluid pathway connector and the needle insertion mechanism.

3. The cartridge of claim 1 wherein the needle of the needle insertion mechanism is in non-axial alignment with the longitudinal axis of the drug container when the carrier is engaged with the fluid pathway connector and the needle insertion mechanism.

4. The cartridge of claim 1 wherein the carrier is removable.

5. The cartridge of claim 1 wherein the fluid pathway connector and the needle insertion mechanism are adapted to remain fluidly coupled by the flexible fluid conduit when the carrier is disengaged from the fluid pathway connector and the needle insertion mechanism.

6. The cartridge of claim 1 wherein the carrier includes a snap connection.

7. The cartridge of claim 1 wherein the carrier includes a threaded connection.

8. The cartridge of claim 1 wherein the carrier includes an interference fit.

9. The cartridge of claim 1 wherein the carrier includes a tongue and groove connection.

10. The cartridge of claim 1 wherein the carrier includes an external support.

11. The cartridge of claim 1 wherein the drug container includes a proximal and a distal end, the cartridge further including a permeable seal disposed at the distal end of the drug container, the fluid pathway connector including a cannula disposed to selectively pierce the permeable seal to fluidly connect the drug container to the needle insertion mechanism.

12. The cartridge of claim 11 wherein the fluid pathway connector is adapted to be assembled to the permeable seal disposed in the drug container.

13. The cartridge of claim 11 wherein the fluid pathway connector is integrated with the permeable seal.

14. The cartridge of claim 1 wherein the carrier includes a tubular housing disposed along at least a portion of the needle insertion mechanism and the fluid pathway connector.

15. The cartridge of claim 14 wherein the carrier includes multiple parts.

16. The cartridge of claim 14 wherein at least a portion of the carrier is removed prior to placement in the drug delivery device.

17. The cartridge of claim 14 wherein at least a portion of the carrier remains with the cartridge when placed in the drug delivery device.

18. The cartridge of claim 14 wherein the carrier surrounds at least a portion of the needle insertion mechanism and the fluid pathway connector.

19. The cartridge of claim 1 wherein the needle insertion mechanism includes an axis extending along the needle, and the drug container and the needle are not in axial alignment when the carrier is disengaged from the fluid pathway connector and the needle insertion mechanism, and the drug container and the needle insertion mechanism are disposed in a drug delivery device.

20. The cartridge of claim 1 wherein the needle insertion mechanism includes an axis extending along the needle, and wherein the drug container and the needle are in axial alignment when the drug container and the needle insertion mechanism are disposed in a drug delivery device.

21. The cartridge of claim 1 wherein the needle insertion mechanism is operative to move the needle to a retracted position following insertion.

22. The cartridge of claim 1 further including a drug contained within the drug container, the cartridge being provided in a sterilized form.

23. The cartridge of claim 1 wherein the drug container includes a plunger seal slidably disposed in a proximal end of the drug container, the plunger seal being axially slidable within the drug container to dispense a drug contained therein through the sterile fluid pathway when the fluid pathway is actuated.

24. A drug delivery device comprising:
a housing,
the cartridge of claim 1 disposed at least partially within the housing, and
an activation mechanism, the activation mechanism being operative to selectively actuate the fluid pathway connector to fluidly connect the drug container to the needle insertion mechanism via the fluid conduit, and actuate the needle insertion mechanism to move the needle to an insertion position.

25. The drug delivery device of claim 24 wherein the activation mechanism and the needle insertion mechanism are operative by a single user action.

26. A method of filling a drug container of a cartridge for use in a drug delivery device, the method comprising:
providing a cartridge according to claim 1, wherein the carrier is engaged with the fluid pathway connector and the needle insertion mechanism; and
subsequently filling the drug container of the cartridge with a pharmaceutical treatment in a sterile environment.

27. The method of claim 26 wherein providing includes sterilizing the cartridge.

28. The method of claim 26 wherein providing includes fluidly coupling the fluid pathway connector and the needle insertion mechanism via the flexible fluid conduit, sterilizing the fluid pathway connector and the needle insertion mechanism, sterilizing the drug container, and engaging the carrier with the fluid pathway connector and the needle insertion mechanism, thereby removably coupling the fluid pathway connector and the needle insertion mechanism together.

29. The method of claim 26 wherein providing includes placing a plurality of cartridges according to claim 1 in a fill finish tray, and sterilizing the plurality of cartridges, and filling includes filling the respective drug containers of the plurality.

30. The method of claim 26 further including assembling a plunger into the filled drug container.

31. An arrangement for use in a fill finish process, the arrangement comprising:
a tray including a plurality of openings, and
a plurality of cartridges of claim 1 disposed in the respective openings.

32. The arrangement of claim 31 wherein the openings are substantially circular openings.

* * * * *

UNITED STATES PATENT AND TRADEMARK OFFICE
CERTIFICATE OF CORRECTION

PATENT NO. : 11,033,679 B2
APPLICATION NO. : 13/798037
DATED : June 15, 2021
INVENTOR(S) : Ian B. Hanson et al.

It is certified that error appears in the above-identified patent and that said Letters Patent is hereby corrected as shown below:

In the Claims

In Claim 1, Column 28 at Line 36 delete "is finable" and insert -- is fillable --.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*